(12) United States Patent
Adje et al.

(10) Patent No.: US 7,754,740 B2
(45) Date of Patent: Jul. 13, 2010

(54) 1H-INDOLE-3-CARBOXYLIC ACID DERIVATIVES AND THEIR USE AS PPAR AGONISTS

(75) Inventors: Nathalie Adje, Genas (FR); Didier Roche, Saclay (FR); Stéphane Yvon, Goyrans (FR)

(73) Assignee: Merck Patent GmbH, Darmstadt (DE)

( * ) Notice: Subject to any disclaimer, the term of this patent is extended or adjusted under 35 U.S.C. 154(b) by 79 days.

(21) Appl. No.: 11/813,922

(22) PCT Filed: Dec. 17, 2005

(86) PCT No.: PCT/EP2005/013634

§ 371 (c)(1),
(2), (4) Date: Jul. 13, 2007

(87) PCT Pub. No.: WO2006/074789

PCT Pub. Date: Jul. 20, 2006

(65) Prior Publication Data

US 2008/0114034 A1    May 15, 2008

(30) Foreign Application Priority Data

Jan. 14, 2005    (FR) .................................. 05 00422

(51) Int. Cl.
- A61K 31/404    (2006.01)
- A61K 31/4439    (2006.01)
- C07D 209/12    (2006.01)
- C07D 401/12    (2006.01)

(52) U.S. Cl. .................... 514/339; 514/419; 546/278.1; 548/492

(58) Field of Classification Search ................. 548/492; 514/419

See application file for complete search history.

(56) References Cited

U.S. PATENT DOCUMENTS

2005/0209282 A1* 9/2005 Wilson et al. ............... 514/320

FOREIGN PATENT DOCUMENTS

WO    WO 02/30895 A    4/2002
WO    WO 02/46154 A    6/2002

OTHER PUBLICATIONS

RN 136038-41-0, retrieved from CAPLUS on Feb. 27, 2009.*
Vippagunta, et al. Advanced Drug Delivery Reviews 48 (2001) pp. 3-26.*
RN 173538-31-3 retrieved from CAPLUS on Jun. 7, 2009.*
RN 64199-47-9 retrieved from CAPLUS on Jun. 7, 2009.*
RN 705257-78-9 from CAPLUS on Jun. 7, 2009.*
RN 851702-19-7 retrieved from CAPLUS on Jun. 7, 2009.*
RN 227029-89-2 retrieved from CAPLUS on Jun. 7, 2009.*
Diabetes Guide [online], [retrieved from the internet on Jun. 17, 2008][URL; http://diabetes.webmd.com/guide/diabetes-overview].*

* cited by examiner

Primary Examiner—Rebecca L Anderson
Assistant Examiner—Shawquia Young
(74) Attorney, Agent, or Firm—Millen, White, Zelano & Branigan, P.C.

(57) ABSTRACT

Compounds of the formula (1): in which A, $R^1$, $R^2$ and $R^3$ are as defined in the description, the processes for the preparation of these compounds, the uses thereof for the treatment of dyslipidaemia, atherosclerosis and diabetes, and the pharmaceutical compositions comprising them.

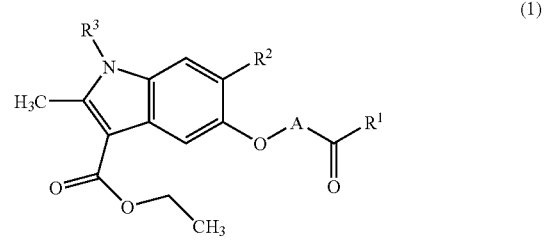

(1)

25 Claims, No Drawings

1H-INDOLE-3-CARBOXYLIC ACID DERIVATIVES AND THEIR USE AS PPAR AGONISTS

The present invention relates to 1 H-indole-3-carboxylic acid derivatives that can be used in the treatment of dyslipidaemia, atherosclerosis and diabetes. The invention also relates to pharmaceutical compositions comprising them and to processes for the preparation of these compounds.

In addition, the invention relates to the use of these compounds for the production of medicaments for the treatment of dyslipidaemia, atherosclerosis and diabetes.

The chronic effect of a calorie imbalance has resulted in an epidemic increase in the incidence of metabolic diseases in modern society. As a result, the World Health Organization has estimated that the global incidence of type 2 diabetes will exceed 300 million in 2030. Although several therapeutic options exist, none of them reverses the progress of this plague.

Although the control of glycated haemoglobin and plasmatic glycaemia in the fasted state are still considered as the primary objectives of antidiabetic treatments, acknowledgement of the fact that the diabetic state encompasses a range of metabolic disorders has broadened scope and expectations of future therapies. In the course of the last decade, hyperglycaemia has been shown to be not the only component of a series of anomalies affecting type-2 diabetic patients. Concurrent diseases, including insulin resistance, obesity, hypertension and dyslipidaemia, which, if they are present together or in part, constitutes what has been described as metabolic syndrome or syndrome X. This array of metabolic disorders forms the bases of a substantial increase in the incidence of cardiovascular disease in these patients.

In the search for novel and improved treatment options for diabetic patients, the family of receptors activated by the peroxisome proliferators ("peroxisome proliferator-activated receptor": PPAR) appears potentially to be an ideal target. This family of ligand-activated transcription factors modulates numerous aspects of lipid and carbohydrate metabolism, thus having the possibility of attacking several facets of the diabetic phenotype. There are three types of PPAR: PPAR alpha, gamma and delta (PPARα, PPARγ and PPARδ, respectively).

PPARα is involved in stimulating the β-oxidation of fatty acids. In rodents, a change transmitted by a PPARα in the expression of genes involved in fatty acid metabolism is the basis of the phenomenon of peroxisome proliferation, a pleiotropic cellular response, mainly limited to the liver and the kidneys, which can lead to hepatocarcinogenesis in rodents. The phenomenon of peroxisome proliferation is not encountered in man. In addition to its role in peroxisome proliferation in rodents, PPARα is also involved in controlling the levels of HDL cholesterol in rodents and humans. This effect is at least partially based on a transcription regulation transmitted by a PPARα of the major HDL apolipoproteins, apo A-I and apo A-II. The hypotriglyceridaemiant action of fibrates and fatty acids also involves PPARα and can be summarised as follows: (i) increased lipolysis and clearance of the remaining particles, due to changes in the levels of lipoprotein lipase and of apo C-III, (ii) stimulation of fatty acid uptake by the cell and its subsequent conversion into acyl-CoA derivatives by induction of a protein for binding fatty acids and acyl-CoA synthase, (iii) induction of the β-oxidation pathways of fatty acids, (iv) reduction in the synthesis of fatty acids and triglycerides, and finally (v) reduction in the production of VLDL. As a result, both the improved catabolism of the triglyceride-rich particles and the reduced secretion of VLDL particles constitute mechanisms that contribute towards the hypolipidaemiant effect of fibrates.

Fibric acid derivatives, such as clofibrate, fenofibrate, benzafibrate, ciprofibrate, beclofibrate and etofibrate, and also gemfibrozil, each of which are PPARα ligands and/or activators, produce a substantial reduction in plasmatic triglycerides and also a certain increase in HDLs. The effects on LDL cholesterol are contradictory and may depend on the compound and/or the dyslipidaemic phenotype. For these reasons, this class of compounds was first used for the treatment of hypertriglyceridaemia (i.e. Fredrickson Type IV and V) and/or mixed hyperlipidaemia.

The activation of a PPARδ was initially reported as not being involved in the modulation of the levels of glucose or of triglycerides (Berger et al., *J. Biol. Chem.*, (1999), Vol. 274, pp. 6718-6725). Later, it was shown that the activation of PPARδ leads to higher levels of HDL cholesterol in dbldb mice (Leibowitz et al., *FEBS Letters*, (2000), 473, 333-336). Furthermore, a PPARδ agonist, during its administration to obese adult insulin-resistant rhesus monkeys, caused a dramatic dose-dependent increase in HDL cholesterol in the serum, while at the same time reducing the levels of low-density LDLs, by depleting the triglycerides and the insulin (Oliver et al., *PNAS*, (2001), 98, 5306-5311). The same publication also showed that the activation of PPARδ increased the Al cassette binding the ATP inverse transporter of cholesterol and induced a flow of cholesterol specific for apolipoprotein A1. Taken together, these observations suggest that the activation of PPARδ is useful for the treatment of and preventing diseases and cardiovascular states comprising atherosclerosis, hypertriglyceridaemia and mixed dyslipidaemia (PCT publication WO 01/00603 (Chao et al.)).

The subtypes of PPARγ receptor are involved in the activation of the programme of adipocyte differentiation and are not involved in the stimulation of peroxisome proliferation in the liver. There are two known isoforms of PPARγ protein: PPARγ1 and PPARγ2, which differ only in the fact that PPARγ2 contains 28 additional amino acids at the amino end. The DNA sequences for the human isotypes are described by Elbrecht et al., *BBRC*, 224, (1996), 431-437. In mice, PPARγ2 is specifically expressed in the fat cells. Tontonoz et al., *Cell*, 79, (1994), 1147-1156, provide proof showing that one physiological role of PPARγ2 is to induce adipocyte differentiation. As with other members of the superfamily of nuclear hormone receptors, PPARγ2 regulates the expression of genes via an interaction with other proteins and binding to hormone response elements, for example in the 5' lateral regions of the response genes. An example of a PPARγ2 response gene is the tissue-specific P2 adipocyte gene. Although peroxisome proliferators, comprising fibrates and fatty acids, activate the transcriptional activity of PPAR receptors, only prostaglandin $J_2$ derivatives have been identified as potential natural ligands of the PPARγ subtype, which also binds antidiabetic thiazolidinedione agents with high affinity.

It is generally thought that glitazones exert their effects by binding to receptors of the family of peroxisome proliferator-activated receptors (PPAR), by controlling certain transcription elements in relation with the biological species listed above. See Hulin et al., *Current Pharm. Design*, (1996), 2, 85-102. In particular, PPARγ has been imputed as a major molecular target for the glitazone class of insulin sensitisers.

Many compounds of glitazone type, which are PPAR agonists, have been approved for use in the treatment of diabetes. These are troglitazone, rosiglitazone and pioglitazone, which are all primary or exclusive agonists of PPARγ.

This indicates that the search for compounds having varying degrees of PPARα, PPARγ and PPARδ activation might lead to the discovery of medicaments that efficiently reduce triglycerides and/or cholesterol and/or glucose, presenting great potential in the treatment of diseases, such as type 2 diabetes, dyslipidaemia, syndrome X (comprising metabolic syndrome, i.e. reduced glucose tolerance, insulin resistance, hypertriglyceridaemia and/or obesity), cardiovascular diseases (comprising atherosclerosis) and hypercholesterolaemia.

The combinations of the PPAR activities that have been studied the most extensively are the PPAR alpha plus gamma combination (dual agonists) with, especially, tesaglitazar, and also the alpha, gamma plus delta triple combination (PPAR-pan agonists).

Although glitazones are beneficial in the treatment of NIDDM, a number of serious unfavourable side effects associated with the use of these compounds have been found. The most serious of these was toxicity to the liver, which has resulted in a certain number of deaths. The most serious problems arose in the use of troglitazone, which has recently been removed from the market for toxicity reasons.

Besides the potential hepatic toxicity of glitazones, other deleterious effects have been associated with PPAR gamma full agonists, for instance weight gain, anaemia and oedema, which limit their use (rosiglitazone, pioglitazone).

On account of the problems that have been encountered with glitazones, researchers in many laboratories have studied classes of PPAR agonists that are not glitazones and do not contain 1,3-thiazolidinedione species, but which modulate the three known subtypes of PPAR, together or separately, to variable degrees (measured by intrinsic power, maximum breadth of functional response or spectrum of changes in gene expression).

Thus, recent studies (cf. WO 01/30343 and WO 02/08188) have revealed that certain compounds have PPAR agonist or partial agonist properties, which are useful in the treatment of type 2 diabetes with reduced side effects with respect to the heart weight and body weight.

The inventors have now discovered a novel class of compounds that are partial or full agonists of PPARγ, with differing degrees of PPARα and/or PPARδ activity.

More specifically, the invention relates to compounds derived from the 1H-indole-3-carboxylic acid of the formula (1) below:

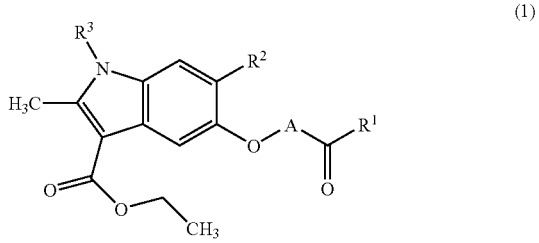

in which:
$R^1$ represents —O—$R'^1$ or —NR'$1_R^{"1}$, with $R'^1$ and $R'''^1$, which may be identical or different, being chosen from a hydrogen atom, an alkyl radical, an alkenyl radical, an alkynyl radical, a cycloalkyl radical, an aryl radical and a heteroaryl radical;
$R^2$ is chosen from:
an alkyl, alkenyl or alkynyl radical;
an aryl radical, optionally substituted and/or optionally fused to a monocyclic or polycyclic, saturated or unsaturated 5- to 8-membered nucleus optionally containing one or more hetero atoms chosen from O, N and S, the said nucleus itself being optionally substituted, and
a saturated, unsaturated or aromatic, optionally substituted 5- to 8-membered monocyclic heterocyclic radical containing one or more hetero atoms chosen from O, N and S;
$R^3$ is chosen from a hydrogen atom and an alkyl radical; and
A represents a linear or branched alkylene chain containing from 1 to 6 carbon atoms;
the possible optical isomers, oxide forms and solvates thereof, and also pharmaceutically acceptable addition salts thereof with acids or bases.

The acids that can be used for the formation of salts of compounds of the formula (1) are mineral or organic acids. The resulting salts are, for example, the hydrochlorides, hydrobromides, sulfates, hydrogen sulfates, dihydrogen phosphates, citrates, maleates, fumarates, trifluoroacetates, 2-naphthalenesulfonates and para-toluenesulfonates.

The bases that can be used for the formation of salts of compounds of the formula (1) are organic or mineral bases. The resulting salts are, for example, the salts formed with metals and especially alkali metals, alkaline-earth metals and transition metals (such as sodium, potassium, calcium, magnesium or aluminium) or with bases, for instance ammonia or secondary or tertiary amines (such as diethylamine, triethylamine, piperidine, piperazine or morpholine) or with basic amino acids, or with osamines (such as meglumine) or with amino alcohols (such as 3-aminobutanol and 2-aminoethanol).

The invention especially encompasses the pharmaceutically acceptable salts, but also salts that allow a suitable separation or crystallisation of the compounds of the formula (1), such as the salts obtained with chiral amines or chiral acids.

Examples of chiral amines that can be used include quinine, brucine, (S)-1-(benzyloxymethyl)propylamine (III), (−)-ephedrine, (4S,5R)-(+)-1,2,3,4-tetramethyl-5-phenyl-1,3-oxazolidine, (R)-1-phenyl-2-p-tolylethylamine, (S)-phenylglycinol, (−)-N-methylephedrine, (+)-(2S,3R)-4-dimethylamino-3-methyl-1,2-diphenyl-2-butanol, (S)-phenylglycinol and (S)-α-methylbenzylamine, or a mixture of two or more thereof.

Examples of chiral acids that can be used include (+)-d-di-O-benzoyltartaric acid, (−)-l-di-O-benzoyltartaric acid, (−)-di-O,O'-p-toluyl-l-tartaric acid, (+)-di-O,O'-p-toluyl-d-tartaric acid, (R)-(+)-malic acid, (S)-(−)-malic acid, (+)-camphanic acid, (−)-camphanic acid, R-(−)-1,1'-binaphthalene-2,2'-diyl hydrogen phosphate, (S)-(+)-1,1'-binaphthalene-2,2'-diyl hydrogen phosphate, (+)-camphoric acid, (−)-camphoric acid, (S)-(+)-2-phenylpropionic acid, (R)-(−)-2-phenylpropionic acid, d-(−)-mandelic acid, l-(+)-mandelic acid, d-tartaric acid and l-tartaric acid, or a mixture of two or more thereof.

The chiral acid is preferably chosen from (−)-di-O,O'-p-toluyl-l-tartaric acid, (+)-di-O,O'-p-toluyl-d-tartaric acid, (R)-(−)-1,1'-binaphthalene-2,2'-diyl hydrogen phosphate, (S)-(+)-1,1'-binaphthalene-2,2'-diyl hydrogen phosphate, d-tartaric acid and L-tartaric acid, or a mixture of two or more thereof.

The invention also encompasses the possible optical isomers, in particular stereoisomers and diastereoisomers, where appropriate, of the compounds of the formula (1), and also mixtures of the optical isomers in any proportions, including racemic mixtures.

Depending on the nature of the substituents, the compounds of the formula (1) may also be in various tautomeric forms, which are also included in the present invention, alone or as mixtures of two or more thereof, in all proportions.

The compounds of the formula (1) above also include the prodrugs of these compounds.

The term "prodrugs" means compounds which, once administered to the patient, are chemically and/or biologically converted by the living body, into compounds of the formula (1).

In the compounds of the formula (1) defined above, the term "alkyl radical" means a linear or branched hydrocarbon-based chain containing from 1 to 10 carbon atoms and better still from 1 to 6 carbon atoms, for example from 1 to 4 carbon atoms.

Examples of alkyl radicals are methyl, ethyl, propyl, isopropyl, butyl, isobutyl, tert-butyl, pentyl, isopentyl, neopentyl, 2-methylbutyl, 1-ethyl-propyl, hexyl, isohexyl, neohexyl, 1-methylpentyl, 3-methylpentyl, 1,1-di-methylbutyl, 1,3-dimethylbutyl, 1-ethylbutyl, 1-methyl-1-ethylpropyl, heptyl, 1-methylhexyl, 1-propylbutyl, 4,4-dimethylpentyl, octyl, 1-methylheptyl, 2-methylhexyl, 5,5-dimethylhexyl, nonyl, decyl, 1-methylnonyl, 3,7-dimethyloctyl and 7,7-dimethyloctyl.

The alkyl radicals present as substituents of the compounds of the formula (1) according to the present invention may be optionally substituted by one or more chemical species chosen from:
 halogen atom;
 —O-alkyl radical;
 aryl radical;
 cycloalkyl radical; and
 heterocyclic radical.

The term "alkylene chain" means a divalent radical of linear or branched aliphatic hydrocarbon-based type derived from the alkyl groups defined above by abstraction of a hydrogen atom. Preferred examples of alkylenediyl chains are —$(CH_2)_k$— chains in which k represents an integer chosen from 1, 2, 3, 4, 5 and 6, and the chains >$CH(CH_3)$, >$C(CH_3)_2$, —$CH_2$—$CH(CH_3)$—$CH_2$— and —$CH_2$—$C(CH_3)_2$—$CH_2$—.

The term "alkenyl radical" means a linear or branched hydrocarbon-based chain containing from 2 to 10 carbon atoms, preferably from 2 to 8 carbon atoms and advantageously from 2 to 6 carbon atoms, containing one, two or more unsaturations in the form of a double bond, the said chain being optionally substituted by one or more substituents, which may be identical or different, chosen from halogen atoms and trifluoromethyl, trifluoromethoxy, hydroxyl, alkoxy, alkoxycarbonyl, carboxyl and oxo radicals.

Examples of alkenyl radicals that may be mentioned include the ethylenyl radical, the propenyl radical, the isopropenyl radical, the but-2-enyl radical, pentenyl radicals and hexenyl radicals.

The term "alkynyl radical" means a linear or branched hydrocarbon-based chain containing from 2 to 10 carbon atoms, preferably from 2 to 8 carbon atoms and advantageously from 2 to 6 carbon atoms, containing one, two or more unsaturations in the form of a triple bond, the said chain being optionally substituted by one or more substituents, which may be identical or different, chosen from halogen atoms and trifluoromethyl, trifluoromethoxy, hydroxyl, alkoxy, alkoxycarbonyl, carboxyl and oxo radicals.

Examples of alkynyl radicals that may be mentioned include the ethynyl radical, the propynyl radical, the but-2-ynyl radical, pentynyl radicals and hexynyl radicals.

According to the invention, the term "aryl radical" means a monocyclic or polycyclic carbocyclic aromatic radical containing from 6 to 18 carbon atoms and preferably from 6 to 10 carbon atoms. Aryl radicals that may be mentioned include phenyl, naphthyl, anthryl and phenanthryl radicals.

In the present invention, the cycloalkyl radical is taken to mean a cyclic hydrocarbon-based radical containing from 4 to 9 carbon atoms, preferably 5, 6 or 7 carbon atoms and advantageously 5 or 6 carbon atoms, optionally containing one or more unsaturations in the form of double and/or triple bonds, the said cycloalkyl radical being optionally substituted by one or more substituents, which may be identical or different, chosen from halogen atoms and alkyl, alkenyl, alkynyl, trifluoromethyl, trifluoromethoxy, hydroxyl, alkoxy, alkoxycarbonyl, carboxyl and oxo radicals.

Preferred examples of cycloalkyl radicals are cyclobutyl, cyclopentyl, cyclopentenyl, cyclohexyl, cyclohexenyl, cyclohexadienyl, cycloheptyl, cycloheptenyl and cycloheptadienyl.

The cycloalkyl radicals are generally monocyclic radicals, but may also be polycyclic, especially bicyclic or tricyclic, optionally containing one or more unsaturations in the form of double bonds.

The polycyclic cycloalkyl radicals are, for example, tetrahydronaphthyl, perhydronaphthyl, indanyl, bicyclooctyl, bicyclononyl and bicyclodecyl radicals.

Unless otherwise indicated, the heterocyclic radicals are monocyclic, bicyclic or tricyclic radicals containing one or more hetero atoms generally chosen from O, S and N, optionally in oxidised form (in the case of S and N), and optionally one or more unsaturations in the form of double bonds. If they are totally saturated, the heterocyclic radicals are said to be aromatic or heteroaryl radicals.

Preferably, at least one of the monocycles constituting the heterocycle contains from 1 to 4 endocyclic hetero atoms and better still from 1 to 3 hetero atoms.

Preferably, the heterocycle consists of one or more monocycles, each of which is 5- to 8-membered.

Examples of 5- to 8-membered monocyclic aromatic heterocyclic radicals are the heteroaryl radicals derived, by abstraction of a hydrogen atom, from aromatic heterocycles, such as pyridine, furan, thiophene, pyrrole, imidazole, thiazole, isoxazole, isothiazole, furazane, pyridazine, pyrimidine, pyrazine, thiazines, oxazole, pyrazole, oxadiazole, triazole and thiadiazole.

Preferred aromatic heterocyclic radicals that may be mentioned include pyridyl, pyrimidinyl, triazolyl, thiadiazolyl, oxazolyl, thiazolyl and thienyl radicals.

Examples of bicyclic heteroaryls in which each monocycle is 5- to 8-membered are chosen from indolizine, indole, isoindole, benzofuran, benzothiophene, indazole, benzimidazole, benzothiazole, benzofurazane, benzothiofurazane, purine, quinoline, isoquinoline, cinnoline, phthalazine, S quinazoline, quinoxaline, naphthyridines, pyrazolotriazines (such as pyrazolo-1,3,4-triazine), pyrazolopyrimidine and pteridine.

Preferred heteroaryl radicals that may be mentioned include the quinolyl, pyridyl, benzothiazolyl and triazolyl radicals.

The tricyclic heteroaryls in which each monocycle is 5- to 8-membered are chosen, for example, from acridine, phenazine and carbazole.

Saturated or unsaturated, 5- to 8-membered monocyclic heterocycles are the saturated or, respectively, unsaturated derivatives of the aromatic heterocycles mentioned above.

More particularly, mention may be made of morpholine, piperidine, thiazolidine, oxazolidine, tetrahydrothienyl, tetrahydrofuryl, pyrrolidine, isoxazolidine, imidazolidine and pyrazolidine.

The aryl and heterocyclic radicals are optionally substituted by one or more of the following radicals G:
 trifluoromethyl; trifluoromethoxy; styryl; halogen atom; monocyclic, bicyclic or tricyclic aromatic heterocyclic radical containing one or more hetero atoms chosen from O, N and S; and optionally substituted by one or more radicals T as defined below; group Het-CO— in which Het represents an aromatic heterocyclic radical as defined above, optionally substituted by one or more radicals T; a $C_1$-$C_6$ alkylene chain; a $C_1$-$C_6$ alkylenedioxy chain; nitro; cyano; ($C_1$-$C_{10}$)alkyl; ($C_1$-$C_{10}$)alkylcarbonyl; $(C_1-C_{10})$alkoxycarbonyl-A- in which A represents $(C_1-C_6)$alkylene, $(C_2-C_6)$alkenylene or a bond; $(C_3-C_{10})$-cycloalkyl; trifluoromethoxy; di$(C_1-C_{10})$alkylamino; $(C_1-C_{10})$alkoxy$(C_1-C_{10})$-alkyl; $(C_1-C_{10})$alkoxy; $(C_6-C_{18})$aryl optionally substituted by one or more radicals T; $(C_6-C_{18})$aryl$(C_1-C_{10})$alkoxy$(CO)_n$— in which n is 0 or 1 and aryl is optionally substituted by one or more radicals T; $(C_6-C_{18})$aryloxy-$(CO)_n$— in which n is 0 or 1 and aryl is optionally substituted by one or more radicals T; $(C_6-C_{18})$arylthio in which aryl is optionally substituted by one or more radicals T; $(C_6-C_{18})$aryloxy$(C_{1-C10})$alkyl$(CO)_n$— in which n is 0 or 1 and aryl is optionally substituted by one or more radicals T; a saturated or unsaturated, 5- to 8-membered monocyclic heterocycle containing one or more hetero atoms chosen from O, N and S, optionally substituted by one or more radicals T; $(C_6-C_{18})$arylcarbonyl optionally substituted by one or more radicals T; $(C_6-C_{18})$arylcarbonyl-B-$(CO)_n$— in which n is 0 or 1; B represents $(C_1-C_6)$-alkylene or $(C_2-C_6)$alkenylene and aryl is optionally substituted by one or more radicals T; $(C_6-C_{18})$aryl-C-$(CO)_n$— in which n is 0 or 1, C represents $(C_1-C_6)$alkylene or $(C_2-C_6)$alkenylene and aryl is optionally substituted by one or more radicals T; $(C_6-C_{18})$aryl fused with a saturated or unsaturated heterocycle as defined above, optionally substituted by one or more radicals T; and $(C_2-C_{10})$alkynyl.

T is chosen from a halogen atom; $(C_6-C_{18})$aryl; $(C_1-C_6)$alkyl; $(C_1-C_6)$alkoxy; $(C_1-C_6)$alkoxy$(C_6-C_{18})$aryl; nitro; carboxyl; $(C_1-C_6)$alkoxycarboxyl; and T may represent oxo if it substitutes a saturated or unsaturated heterocycle; or alternatively T represents $(C_1-C_6)$alkoxycarbonyl$(C_1-C_6)$alkyl; or $(C_1-C_6)$alkylcarbonyl$((C_1-C_6)$alkyl),- in which n is 0 or 1.

The term "halogen atom" means a chlorine, bromine, iodine or fluorine atom, preferably fluorine or chlorine.

Among the compounds of the formula (1), the ones that are preferred are those for which $R^1$ represents —O—$R'^1$ and most particularly those for which $R^1$ represents —O—$R'^1$, $R'^1$ being a hydrogen atom or an alkyl radical.

A first preferred group of compounds of the invention consists of compounds having one or more of the following characteristics, taken separately or as a combination of one, several or all of them:

$R^1$ represents —O—$R'^1$, $R'^1$ being chosen from a hydrogen atom and an alkyl radical;

$R^2$ represents an alkyl radical optionally substituted by a radical —O-alkyl, aryl or cycloalkyl, or alternatively represents an optionally substituted aryl radical, or alternatively an optionally substituted heterocyclic radical;

$R^3$ is chosen from a hydrogen atom and an alkyl radical optionally substituted by a radical —O-alkyl, aryl or cycloalkyl; and A represents a linear or branched alkylene chain containing from 1 to 6 carbon atoms;

the possible optical isomers, oxide forms and solvates thereof, and also pharmaceutically acceptable addition salts thereof with acids or bases.

Another even more preferred group of compounds of the invention consists of compounds having one or more of the following characteristics, taken separately or as a combination of one, several or all of them:

$R^1$ represents —O—$R'^1$, $R'^1$ being chosen from a hydrogen atom and an alkyl radical containing from 1 to 6 carbon atoms;

$R^2$ represents an alkyl radical containing from 1 to 6 carbon atoms and optionally substituted by a radical —O-alkyl containing from 1 to 6 carbon atoms, or substituted by a phenyl radical or a 5- or 6-membered cycloalkyl radical, or alternatively represents an optionally substituted phenyl radical, or alternatively an optionally substituted heterocyclic radical;

$R^3$ is chosen from a hydrogen atom and an alkyl radical containing from 1 to 6 carbon atoms and optionally substituted by a radical —O-alkyl containing from 1 to 6 carbon atoms, or substituted by a phenyl radical or a 5- or 6-membered cycloalkyl radical; and A represents a linear or branched alkylene chain containing from 1 to 6 carbon atoms;

the possible optical isomers, oxide forms and solvates thereof, and also pharmaceutically acceptable addition salts thereof with acids or bases.

Another preferred group of compounds of the invention consists of compounds having one or more of the following characteristics, taken separately or as a combination of one, several or all of them:

$R^1$ represents —O—$R'^1$, $R'^1$ being chosen from a hydrogen atom, a methyl radical and an ethyl radical;

$R^2$ represents an alkyl radical containing from 1 to 6 carbon atoms and optionally substituted by a methoxy or ethoxy radical, or substituted by a substituted phenyl radical or a cyclopentyl or cyclohexyl radical, or alternatively represents an optionally substituted phenyl radical, or alternatively an optionally substituted aromatic heterocyclic radical containing at least one nitrogen atom;

$R^3$ is chosen from a hydrogen atom and an alkyl radical containing from 1 to 6 carbon atoms and optionally substituted by a methoxy or ethoxy radical, or substituted by a substituted phenyl radical or a cyclopentyl or cyclohexyl radical; and A represents an alkylene chain of the formula —$(CH_2)_k$—, in which k represents an integer between 1 and 6, limits inclusive, or a —$C(CH_3)_2$— chain;

the possible optical isomers, oxide forms and solvates thereof, and also pharmaceutically acceptable addition salts thereof with acids or bases.

Another even more preferred group of compounds of the invention consists of compounds having one or more of the following characteristics, is taken separately or as a combination of one, several or all of them:

$R^1$ represents a hydrogen atom;

$R^2$ is chosen from methyl, ethyl, propyl and n-hexyl radicals, optionally substituted by a methoxy or ethoxy radical, or substituted by a substituted phenyl radical, or with a cyclopentyl radical, or alternatively represents an optionally substituted phenyl radical, or alternatively an optionally substituted pyridyl radical;

$R^3$ is chosen from a hydrogen atom, a methyl radical, an ethyl radical, a propyl radical, an isopropyl radical, an isobutyl radical and an isopentyl radical, each of these radicals being optionally substituted by a methoxy or ethoxy radical, or with a substituted phenyl radical; and A represents an alkylene chain of the formula —$(CH_2)_k$—, in which k represents 1, 2 or 3, or a —$C(CH_3)_2$— chain;

the possible optical isomers, oxide forms and solvates thereof, and also pharmaceutically acceptable addition salts thereof with acids or bases.

The substituents on the aryl and heterocyclic radicals are preferably chosen from halogen atoms, preferably fluorine and/or chlorine, and methyl, ethyl, methoxy, phenyl, trifluoromethyl and trifluoromethoxy radicals.

The heterocyclic radicals are preferentially chosen from thienyl, benzothiophenyl, pyridyl and oxazolyl radicals.

More particularly, the preferred compounds of the formula (1) are those chosen from:

ethyl 1-benzyl-5-(3-carboxypropoxy)-2-methyl-6-pyrid-3-yl-1H-indole-3-carboxylate;

ethyl 5-(3-carboxypropoxy)-1-(4-chlorobenzyl)-2-methyl-6-pyrid-3-yl-1H-indole-3-carboxylate;

ethyl 5-(1-carboxy-1-methylethoxy)-2-methyl-1-(3-methylbutyl)-6-pyrid-4-yl-1H-indole-3-carboxylate;

ethyl 5-carboxymethoxy-6-hexyl-1-isobutyl-2-methyl-1H-indole-3-carboxylate;

ethyl 5-carboxymethoxy-6-(3-ethoxypropyl)-1-isobutyl-2-methyl-1H-indole-3-carboxylate;

ethyl 5-carboxymethoxy-6-(3-cyclopentylpropyl)-1-(2-methoxyethyl)-2-methyl-1H-indole-3-carboxylate;

ethyl 5-carboxymethoxy-6-[2-(4-fluorophenyl)ethyl]-1-(2-methoxyethyl)-2-methyl-1H-indole-3-carboxylate;

ethyl 5-(3-carboxypropoxy)-6-hexyl-1-(2-methoxyethyl)-2-methyl-1H-indole-3-carboxylate;

ethyl 5-(3-carboxypropoxy)-6-(3-ethoxypropyl)-1-(2-methoxyethyl)-2-methyl-1H-indole-3-carboxylate; and ethyl 5-(3-carboxypropoxy)-6-(3-cyclopentylpropyl)-1-(2-methoxyethyl)-2-methyl-1H-indole-3-carboxylate;

and the possible optical isomers, oxide forms and solvates thereof, and also pharmaceutically acceptable addition salts of these compounds with acids or bases.

The invention also relates to pharmaceutical compositions comprising a pharmaceutically effective amount of at least one compound of the formula (1) as defined above in combination with one or more pharmaceutically acceptable vehicles.

These compositions can be administered orally in the form of tablets, gel capsules or granules with immediate release or controlled release, intravenously in the form of an injectable solution, transdermally in the form of an adhesive transdermal device, or locally in the form of a solution, cream or gel.

A solid composition for oral administration is prepared by adding to the active principle a filler and, where appropriate, a binder, a disintegrant, a lubricant, a dye or a flavour enhancer, and by forming the mixture into a tablet, a coated tablet, a granule, a powder or a capsule.

Examples of fillers include lactose, corn starch, sucrose, glucose, Is sorbitol, crystalline cellulose and silicon dioxide, and examples of binders include poly(vinyl alcohol), poly(vinyl ether), ethylcellulose, methylcellulose, acacia, gum tragacanth, gelatine, shellac, hydroxypropylcellulose, hydroxypropylmethylcellulose, calcium citrate, dextrin and pectin. Examples of lubricants include magnesium stearate, talc, polyethylene glycol, silica and hardened plant oils. The dye can be any dye permitted for use in medicaments. Examples of flavour enhancers include cocoa powder, mint in herb form, aromatic powder, mint in oil form, borneol and cinnamon powder. Needless to say, the tablet or granule may be appropriately coated with sugar, gelatine or the like.

An injectable form comprising the compound of the present invention as active principle is prepared, where appropriate, by mixing the said compound with a pH regulator, a buffer, a suspending agent, a solubilising agent, a stabiliser, a tonicity agent and/or a preserving agent, and by converting the mixture into a form for intravenous, subcutaneous or intramuscular injection according to a standard process. Where appropriate, the injectable form obtained can be freeze-dried via a standard process.

Examples of suspending agents include methylcellulose, polysorbate 80, hydroxyethylcellulose, acacia, powdered gum tragacanth, sodium carboxymethyl cellulose and polyethoxylated sorbitan monolaurate.

Examples of solubilising agents include castor oil solidified with polyoxyethylene, polysorbate 80, nicotinamide, polyethoxylated sorbitan monolaurate and the ethyl ester of castor oil fatty acid.

In addition, the stabiliser encompasses sodium sulfite, sodium metasulfite and ether, while the preserving agent encompasses methyl p-hydroxybenzoate, ethyl p-hydroxybenzoate, sorbic acid, phenol, cresol and chlorocresol.

The present invention also relates to the use of a compound of the formula (1) of the invention for the preparation of a medicament for the prevention or treatment dyslipidaemia, atherosclerosis and diabetes.

The effective administration doses and posologies of the compounds of the invention, intended for the prevention or treatment of a disease, condition or state caused by or associated with modulation of the activity of the PPARs, depends on a large number of factors, for example on the nature of the modulator, the size of the patient, the desired aim of the treatment, the nature of the pathology to be treated, the specific pharmaceutical composition used and the observations and conclusions of the treating doctor.

For example, in the case of an oral administration, for example, a tablet or a gel capsule, a possible suitable dosage of the compounds of the formula (1) is between about 0.1 mg/kg and about 100 mg/kg of body weight per day, preferably between about 0.5 mg/kg and about 50 mg/kg of body weight per day, more preferentially between about 1 mg/kg and about 10 mg/kg of body weight per day and more preferably between about 2 mg/kg and about 5 mg/kg of body weight per day of active material.

If representative body weights of 10 kg and 100 kg are considered in order to illustrate the daily oral dosage range that can be used and as described above, suitable dosages of the compounds of the formula (1) will be between about 1-10 mg and 1000-10 000 mg per day, preferably between about 5-50 mg and 500-5000 mg per day, more preferably between about 10.0-100.0 mg and 100.0-1000.0 mg per day and even more preferentially between about 20.0-200.0 mg and about 50.0-500.0 mg per day of active material comprising a preferred compound.

These dosage ranges represent total amounts of active material per day for a given patient. The number of administrations per day at which a dose is administered may vary within wide proportions as a function of pharmacokinetic and pharmacological factors, such as the half-life of the active material, which reflects its rate of catabolism and of clearance, and also the minimum and optimum levels of the said active material reached in the blood plasma or other bodily fluids of the patient and which are required for therapeutic efficacy.

Many other factors should also be considered in deciding upon the number of daily administrations and the amount of active material that should be administered at a time. Among these other factors, and not the least of which, is the individual response of the patient to be treated.

The present invention also relates to a general process for the preparation of the compounds of the formula (1), starting with ethyl 6-bromo-5-hydroxy-2-methyl-1H-indole-3-carboxylate, the hydroxyl function of which is subjected to the action of a compound of the formula (2):

$$Br\text{-}A\text{-}CO_2R \qquad (2)$$

in which A is as defined above for the compounds of the formula (1) and R represents a protecting group for the acid function, for example an alkyl radical, such as methyl or ethyl, in the presence of a base, such as an alkali metal or alkaline-earth metal hydroxide or carbonate, for example sodium hydroxide or potassium carbonate ($K_2CO_3$), in polar aprotic medium, for example in dimethylformamide (DMF) solvent, to give the compound of the formula (3):

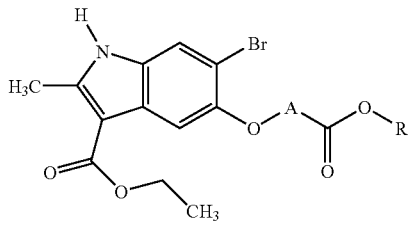
(3)

in which A and R are as defined above, of which compound of the formula (3) the nitrogen atom may optionally be substituted, under the action of a bromide $R^3$—Br, in which $R^3$ is as defined for the compounds of the formula (1), under conditions similar to those outlined above (for example NaOH or $K_2CO_3$/DMF), so as to obtain the compound of the formula (4):

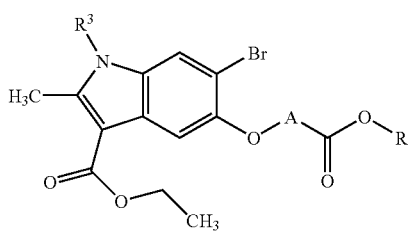
(4)

in which A, $R^3$ and R are as defined above, and then subjected to a Heck reaction (R. F. Heck et al., *J. Org. Chem.*, (1972), 37, 2320 sqq.) in which a compound of the formula R'—CH=CH—R" (precursor of the radical $R^2$—, radical $R^2$— possibly being represented by the radical R'—CH$_2$—CH—R") is treated with a borane, for example 9-borabicyclo[3.3.1]nonane, to give an $R^2$-borane, in which $R^2$ is as defined for the compounds of the formula (1), which is then coupled with the compound of the formula (3), in the presence of a palladium catalyst, such as 1,1'-bis(diphenylphosphino)ferrocenedichloropalladium II $PdCl_2dppf$), in basic medium, for example in potassium phosphate, in a polar aprotic solvent, for instance tetrahydrofuran, to give the compound of the formula ($1_R$):

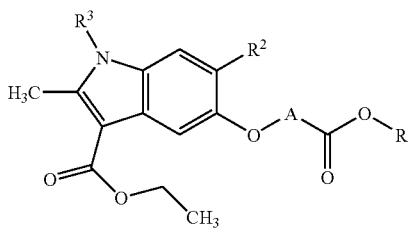
($1_R$)

in which A, $R^2$, $R^3$ and R are as defined above, which compound of the formula ($1_R$) is then converted, according to standard techniques known to those skilled in the art, into the corresponding acid of the formula ($1_{OH}$):

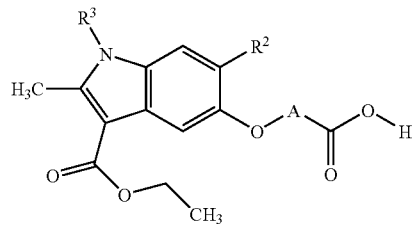
($1_{OH}$)

which is a special case of the compounds of the formula (1) in which $R^1$ represents a hydroxyl group, and the acid is optionally esterified, or converted into the corresponding amide, also according to standard techniques, to form the set of compounds of the formula (1), with $R^1$ other than a hydroxyl group.

This synthetic method applies to all the compounds of the formula (1) according to the present invention, and is described in greater detail in the synthesis of the compounds of Examples 1, 2, 12 and 13 below.

It should be understood that the compounds of the formula ($1_R$) above, if R represents an alkyl radical, form part of the compounds of the formula (1) according to the present invention.

If such compounds are desired, the steps of deprotection of the acid function and then of esterification are superfluous.

According to one variant, the compounds of the formula (1) can also be prepared from ethyl 6-bromo-5-hydroxy-2-methyl-1H-indole-3-carboxylate, the hydroxyl function of which is protected in a conventional manner, for example by reaction with acetic anhydride, in the presence of pyridine, and the nitrogen atom is then optionally substituted, under the action of a bromide $R^3$—Br, as indicated for the production of compound (4) defined above, and the hydroxyl function is then deprotected, in the presence of a base and in an alcohol, for example sodium hydroxide in methanol, so as to obtain the compound of the formula (5):

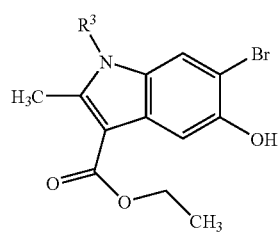
(5)

in which $R^3$ is as defined above, for which compound of the formula (5) the synthesis up to the compound of the formula (1) is continued by means of a technique of synthesis on resin, for example of grafted Wang type and corresponding to formula (6):

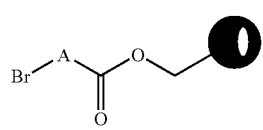
(6)

in which A is as defined for the compounds of the formula (1) and ● represents the resin support, which, when placed in contact with compound (5), in basic medium and a polar aprotic solvent, for example K$_2$CO$_3$/DMF, in the presence of potassium iodide, gives the compound of the formula (7):

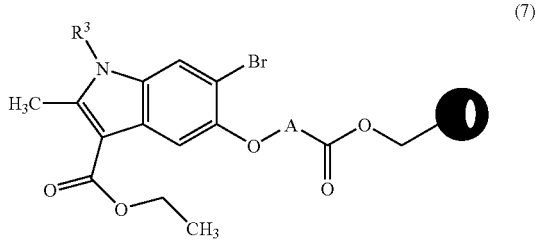

(7)

in which A, R$^3$ and ●are as defined above, the bromine atom of which is replaced with the substituent R$^2$, under the same operating conditions as those described above for the production of the compound of the formula (1$_R$), thus leading to the compound of the formula (8):

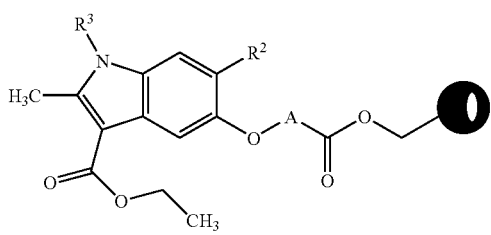

(8)

in which A, R$^2$, R$^3$ and ●are as defined above, which is then detached from the resin support according to the usual conditions, for example using trifluoroacetic acid, so as to give the compound of the formula (1$_{OH}$) described above, which is then, where appropriate, esterified or converted into the corresponding amide, to form the set of compounds of the formula (1) with R$^1$ other than a hydroxyl group.

This method is more particularly detailed in the preparation of the compounds of Examples 3, 14-17 and 29-31.

According to one alternative, the attachment to the grafted resin (6) can be performed directly on ethyl 6-bromo-5-hydroxy-2-methyl-1H-indole-3-carboxylate, so as to obtain the bromo derivative of the formula (9):

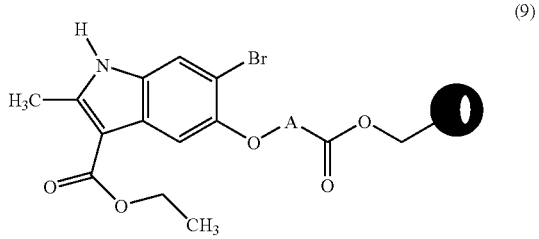

(9)

in which A and ●are as defined above,
in which derivative of the formula (9) the nitrogen atom may be optionally substituted by the radical R$^3$, and the bromine atom replaced with the radical R$^2$ (in any order), according to the techniques outlined above for the preparations of the compounds of the formulae (5) and (8), respectively.

This method is more particularly detailed in the preparation of the compounds of Examples 4-11 and 18-28.

The compounds of the formula (1) in which R$^1$ represents H can advantageously be obtained by saponification of the corresponding compounds of the formula (1) in which R$^1$ represents an alkyl radical, or alternatively starting with the compounds of the formula (1$_R$), in which R represents an alkyl radical. The saponification can be performed via the action of a base, such as a mineral base chosen from lithium hydroxide, potassium hydroxide, sodium hydroxide, sodium hydrogen carbonate, potassium hydrogen carbonate, sodium carbonate and potassium carbonate. The molar amount of base to be used generally ranges from 1 to 20 equivalents and preferably from 1 to 12 equivalents depending on the strength of the selected base.

The reaction is preferably performed in a solvent of polar protic type and more preferably in a mixture of a lower (C$_1$-C$_4$) alkanol and water, such as a mixture of ethanol and water or methanol and water.

The reaction temperature advantageously ranges between room temperature and 120° C. and better still between 20° C. and 100° C., for example between 20° C. and reflux.

The compound of the formula (6) can readily be obtained by coupling a resin of Wang type, of the formula (10), with an acid of the formula (11), according to the following reaction scheme:

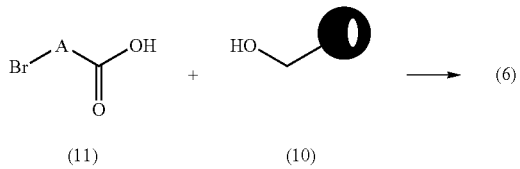

(11)     (10)

in which A is as defined for the compounds of the formula (1) and ●represents the resin support,
according to standard techniques known to those skilled in the art, for example in the presence of 4-dimethylaminopyridine (DMAP) and N,N'-diisoproplcarbodiimide (DIC), in apolar organic medium, for example in methylene chloride.

This grafting of the Wang resin is described in greater detail in Example 3, step 4.

In the processes described above, it should be understood that the operating conditions may vary substantially as a function of the various substituents present in the compounds of the formula (1) that it is desired to prepare. Such variations and adaptations are readily accessible to those skilled in the art, for example from scientific reviews, the patent literature, Chemical Abstracts, and computer databases, including the Internet. Similarly, the starting materials are either commercially available or accessible via syntheses that a person skilled in the art can readily find, for example in the various publications and databases described above.

The optical isomers of the compounds of the formula (1) can be obtained on the one hand via standard techniques for separating and/or purifying isomers known to those skilled in the art, starting with the racemic mixture of the compound of the formula (1). The optical isomers can also be obtained directly via stereoselective synthesis of an optically active starting compound, or via separation or recrystallisation of the optically active salts of the compounds of the formula (1), the salts being obtained with chiral amines or chiral acids.

The examples that follow illustrate the present invention without limiting it in any way. In these examples and the proton nuclear magnetic resonance data (300 MHz NMR), the following abbreviations have been used: s for singlet, d for doublet, t for triplet, q for quartet, o for octet and m for complex multiplet. The chemical shifts δ are expressed in ppm.

EXAMPLES

Example 1

Ethyl 5-ethoxycarbonylmethoxy-6-hexyl-1-isobutyl-2-methyl-1H-indole-3-carboxylate Step 1

A mixture of ethyl 6-bromo-5-hydroxy-2-methyl-1H-indole-3-carboxylate (5 g; 16.77 mmol), ethyl 2-bromoacetate (4.2 g; 25.16 mmol) and potassium carbonate (2.3 g; 16.89 mmol) in dimethylformamide (DMF) (20 ml) is heated at 60° C. for 1 hour 30 minutes. The reaction medium is poured into a mixture of ice and ethyl acetate. The aqueous phase is extracted twice with ethyl acetate. The combined organic phases are washed with water, dried over sodium sulfate and then concentrated. The residue obtained (6.85 g) is purified by chromatography on silica (3.63 g; 57%).

$^1$H NMR (300 MHz, chloroform-D), δ ppm: 1.2 (t, J=6.9 Hz, 3 H); 1.4 (t, J=7.2 Hz, 3 H); 2.6 (s, 3 H); 4.2 (m, 4 H); 4.7 (s, 2 H); 7.2 (s, 1 H); 7.3 (s, 1 H); 7.5 (s, 1 H).

Step 2

A mixture of the compound obtained in step 1 (3.63 g; 9.45 mmol), isobutyl bromide (2.6 g; 18.98 mmol) and potassium carbonate (2.68 g; 19.68 mmol) in DMF (20 ml) is heated for 48 hours. A large excess of the halide, of potassium carbonate and of potassium iodide (0.615 mg) is added and the mixture is heated for a further 48 hours. The reaction medium is then poured into a mixture of ice and ethyl acetate. The aqueous phase is extracted twice with ethyl acetate. The combined organic phases are washed with water, dried over sodium sulfate and then concentrated. The residue obtained (3.73 g) is purified by chromatography on silica (gradient: 0-30% ethyl acetate in heptane). 1.73 g (42%) of the expected product are obtained.

$^1$H NMR (300 MHz, chloroform-D), δ ppm: 0.9 (d, J=6.7 Hz, 6 H); 1.3 (t, J=7.2 Hz, 3 H); 1.4 (t, J=7.2 Hz, 3 H); 2.2 (m, 1 H); 2.7 (s, 3 H); 3.8 (d, J=7.8 Hz, 2 H); 4.3 (q, J=7.2 Hz, 2 H); 4.4 (q, J=7.2 Hz, 2 H); 4.7 (s, 2 H); 7.5 (s, 1 H); 7.6 (s, 1 H).

Step 3

Preparation of the organoborane solution: a solution of hexene (0.42 g; 5 mmol) in tetrahydrofuran (THF) (2 ml) is cooled under nitrogen to 3° C. A commercial 0.5 N solution of 9-borabicyclo[3.3.1]nonane (9-BBN) in THF (10 ml, 5 mmol) is then added dropwise so as to keep the temperature below 5° C. The colourless solution obtained is then stirred for 3 hours at room temperature.

A mixture of the compound obtained in step 2 (0.208 g; 0.47 mmol), PdCl$_2$dppf (12.3 mg; 15.1 μmol) and potassium phosphate (237 mg; 0.89 mmol) in THF (2 ml) is refluxed and the organoborane solution (2.3 ml; 0.96 mmol) is then added in a single portion. The medium, which quickly turns black, is refluxed for 1 hour 30 minutes. The reaction medium is then poured into a mixture of water and ethyl ether. The aqueous phase is extracted. The combined organic phases are washed with water, dried over sodium sulfate and then concentrated.

The oily residue obtained (0.5 g) is purified by chromatography on silica (4/1 heptane/ethyl acetate) and then dispersed in heptane (82.0 mg; 39%).

$^1$H NMR (300 MHz, chloroform-D), δ ppm: 0.9 (t, J=6.7 Hz, 3 H); 0.9 (d, J=6.7 Hz, 6 H); 1.4 (m, 6 H); 1.3 (t, J=7.2 Hz, 3 H); 1.4 (t, J=7.2 Hz, 3 H); 1.7 (m, 2 H); 2.2 (s, 1 H); 2.8 (m, 2 H); 2.7 (s, 3 H); 3.9 (d, J=7.4 Hz, 2 H); 4.3 (q, J=7.2 Hz, 2 H); 4.4 (q, J=7.2 Hz, 2 H); 4.7 (s, 2 H); 7.0 (s, 1 H); 7.5 (s, 1 H).

Example 2

Ethyl 5-carboxymethoxy-6-hexyl-1-isobutyl-2-methyl-1H-indole-3-carboxylate

A mixture of the compound obtained in Example 1 (82.0 mg; 0.184 mmol), methanol (2 ml) and aqueous 1 N sodium hydroxide (0.265 ml; 0.265 mmol) is stirred overnight at room temperature. The solvents are evaporated off. The residue is dissolved in water and then treated with concentrated hydrochloric acid. After extraction with ethyl ether and drying over sodium sulfate, evaporation gives a white solid (71 mg; 92%).

$^1$H NMR (300 MHz, chloroform-D), δ ppm: 0.9 (m, 3 H); 0.9 (d, J=6.7 Hz, 6 H); 1.3 (m, 7 H); 1.4 (t, J=7.2 Hz, 3 H); 1.6 (m, 2 H); 2.2 (m, 1 H); 2.8 (m, 2 H); 2.7 (s, 3 H); 3.9 (d, J=7.6 Hz, 2 H); 4.4 (q, J=7.2 Hz, 2 H). 4.7 (s, 2 H); 7.0 (s, 1 H); 7.5 (s, 1 H).

Example 3

Ethyl 5-(3-carboxypropoxy)-6-hexyl-1-(2-methoxyethyl)-2-methyl-1H-indole-3-carboxylate Step 1

A mixture composed of ethyl 6-bromo-5-hydroxy-2-methyl-1H-indole-3-carboxylate (14.91 g; 50 mmol), acetic anhydride (100 ml; 1.06 mol) and pyridine (12.08 ml; 0.15 mol) is refluxed for one hour. The cooled reaction medium is then poured into saturated sodium bicarbonate solution. After extraction with ethyl acetate, the combined organic phases are washed with water, dried over sodium sulfate and then concentrated. The residue obtained (14.0 g) is dispersed in methylene chloride (8.3 g). The mother liquors, concentrated and then chromatographed on a column of alumina (methylene chloride), give a further amount of the expected product (2.9 g). The two batches (8.3 g and 2.9 g) are combined and dispersed in ethyl ether. 9.6 g of pure product are obtained.

Melting point: 200° C.

$^1$H NMR (300 MHz, chloroform-D), δ ppm: 1.4 (t, J=7.1 Hz, 3 H); 2.4 (s, 3 H); 2.6 (s, 3 H); 4.4 (q, J=7.1 Hz, 2 H); 7.3 (s, 1 H); 7.7 (s, 1 H); 8.6 (s, 1 H).

Step 2

A mixture composed of the derivative obtained in step 1 (9.05 g; 26.60 mmol), sodium hydroxide (NaOH) (1.17 g; 29.26 mmol) and 2-methoxyethyl bromide (7.50 ml; 79.81 mmol) in dry DMF is stirred at 40° C. for 4 hours. The cooled reaction medium is then poured into ice-cold dilute hydrochloric acid. After extraction with ethyl acetate, the combined organic phases are washed with water and dried over sodium sulfate. The evaporation residue is dispersed in pentane (7.84 g).

$^1$H NMR (300 MHz, chloroform-D), δ ppm: 1.4 (t, J=7.1 Hz, 3 H); 2.4 (s, 3 H); 2.8 (s, 3 H); 3.3 (s, 3 H); 3.6 (t, J=5.5 Hz, 2 H); 4.2 (t, J=5.5 Hz, 2 H); 4.4 (q, J=7.1 Hz, 2 H); 7.5 (s,1 H); 7.8 (s, 1 H).

Step 3

A mixture composed of the derivative obtained in step 2 (7.81 g; 19.61 mmol) and aqueous 1 N sodium hydroxide (23.5 ml; 23.5 mmol) in methanol (80 ml) is stirred at room temperature for 1 hour. The reaction medium is then poured into dilute hydrochloric acid. The precipitate formed is filtered off, washed and drained by suction (6.65 g; 90%).

Melting point: 195° C.

$^1$H NMR (300 MHz, chloroform-D), δ ppm: 1.4 (t, J=7.2 Hz, 3 H); 2.8 (s, 3 H); 3.3 (s, 3 H); 3.6 (t, J=5.6 Hz, 2 H); 4.2 (t, J=5.6 Hz, 2 H); 4.4 (q, J=7.2 Hz, 2 H); 5.3 (s, 1 H); 7.4 (s, 1 H); 7.7 (s, 1 H).

Step 4

Grafting of 4-bromobutyric acid onto the Wang resin:

A mixture composed of Wang resin (8.24 g; 0.91 mM/g), 4-bromobutyric acid (5.51 g; 33 mmol), 4-dimethylaminopyridine (DMAP) (0.183 g; 1.5 mM) and N,N'-diisopropylcarbodiimide (DIC) (5.14 g; 33 mmol) in methylene chloride (130 ml) is stirred with an orbital stirrer for 20 hours in a 250 ml flask. The resin is washed three times with methylene chloride and then three times with methanol. After drying under vacuum at room temperature, 9.16 g of grafted resin are obtained (theory: 9.36 g).

2.63 g of the above resin are taken and poured into dry DMF (14 ml). The 5-hydroxy-6-bromoindole derivative obtained in step 3 (1.5 g; 4.21 mmol), potassium iodide (349.5 mg; 2.1 mmol) and potassium carbonate (291 mg; 2.1 mmol) are then successively added. The mixture is heated at 80° C. overnight. The resin is filtered off and washed three times with DMF (5 ml), then three times with a 1/1 tetrahydrofuran/water mixture (5 ml), then three times with tetrahydrofuran (5 ml) and then three times with methanol (5 ml) and finally dried under vacuum (3.14 g, theory: 3.21 g).

Step 5

Preparation of the organoborane solution: a 0.5 N solution of 9-BBN in THF (1.2 ml; 0.60 mmol) is cooled to 0° C. and hexene (75 μl; 0.60 mmol) is then added. The colourless solution obtained is then stirred for three hours at room temperature.

The organoborane solution (0.957 ml; 0.45 mmol) is added to a mixture of resin obtained in step 4 (227.27 mg), Pd(PPh$_3$)$_4$ (8.67 mg; 75.0 μmol) and aqueous 2 M sodium carbonate (94 μl; 188 μmol) in DMF (2 ml). The medium is heated at 80° C. overnight. The resin is filtered off and washed three times with DMF, then three times with a 1/1 tetrahydrofuran/water mixture, three times with methanol and then three times with methylene chloride and finally dried under vacuum.

Step 6

The resin obtained in step 5 is treated for 2 hours at room temperature with an 8/2 mixture of methylene chloride/trifluoroacetic acid (2 ml).

The medium is filtered and the resin is then washed with methylene chloride. The filtrate is concentrated to dryness (10 mg). The resin is then treated again for 2 hours with a 1/1 mixture of methylene chloride/trifluoroacetic acid.

After filtration and washing, evaporation of the filtrate gives an additional 18 mg of product (total 28 mg).

$^1$H NMR (300 MHz, chloroform-D), δ ppm: 0.9 (m, 3 H); 1.3 (m, 6 H); 1.4 (t, J=7.2 Hz, 3 H); 1.6 (m, 2 H); 2.2 (m, 2 H); 2.7 (m, 7 H); 3.3 (s, 3 H); 3.6 (t, J=5.7 Hz, 2 H); 4.1 (t, J=5.8 Hz, 2 H); 4.3 (t, J=5.6 Hz, 2 H); 4.4 (m, 2 H); 5.3 (s, 1 H) 7.0 (s, 1 H); 7.6 (s,1 H).

LC/MS: ES+448.5 ES-446.4

Example 4

Ethyl -benzyl-5-(3-carboxypropoxy)-2-methyl-6-pyrid-3-yl-1H-indole-3-carboxylate Step 1

2.85 g of grafted Wang resin (loading 1.09 mM/g) are taken up with 4-bromobutyric acid (preparation identical to that described in step 4 of Example 3, but starting with a 1.3 mM/g Wang resin) and poured into dry DMF (58 ml). Next, ethyl 6-bromo-5-hydroxy-2-methyl-1H-indole-3-carboxylate (3.71 g; 12.44 mmol), potassium iodide (0.52 g; 3.13 mmol) and potassium carbonate (0.43 g; 3.11 mmol) are successively added. The mixture is heated at 80° C. for 16 hours. The resin is filtered off and washed twice with DMF, three times with a 1/1 tetrahydrofuran/water mixture, three times with tetrahydrofuran (THF) and three times with methanol and finally dried under vacuum (3.37 g, theory: 3.52 g).

Step 2

602 mg of the above resin (loading 0.88 mM/g) in DMF (5 ml) are treated with sodium hydride (NaH) at 60% in oil (63.3 mg; 1.58 mmol) for 15 minutes, and potassium iodide (88 mg; 0.53 mmol) and benzyl bromide (362.6 mg; 2.11 mmol) are then added. The mixture is stirred for 20 hours at room temperature under nitrogen.

Ethyl acetate (0.5 ml) is added and the resin is then filtered off and washed three times with DMF (10 ml), three times with 1/1 THF/H$_2$O, three times with THF and three times with methanol and finally dried under vacuum.

Step 3

A mixture of the above resin (146.3 mg; loading 0.82 mM/g), PdP(Ph$_3$)$_4$ (27.7 mg; 24 μmol), aqueous 2 M sodium carbonate (120 μl; 240 mmol) and 3-pyridylboronic acid (59 mg; 480 μmol) in DMF (2 ml) is heated at 120° C. for 12 hours. The mixture is stirred for 20 hours at room temperature under nitrogen.

The resin is filtered off and washed three times with DMF (2 ml), three times with 1/1 THF/H$_2$O, three times with THF, three times with methanol and three times with methylene chloride and finally dried under vacuum.

The resin obtained is treated with an 8/2 mixture of methylene chloride/trifluoroacetic acid (1.5 ml) for 1.5 hours at room temperature.

The medium is filtered and the resin is then washed with methylene chloride. The filtrate is concentrated to dryness (39 mg).

LC/MS: ES+473.2

Example 5

Ethyl 5-(3-carboxypropoxy)-2-methyl-6-(3,4-dichlorophenyl)-1H-indole-3-carboxylate A mixture of the resin obtained in step 1 of Example 4 (144 mg; loading 0.94 mmol/g), a 0.025 M solution of PdP(Ph$_3$)$_4$ in DMF (1 ml; 25 μmol), aqueous 2M sodium carbonate (135 μl; 270 mmol) and 3,4-di-chlorophenylboronic acid (52 mg; 270 μmol) in DMF (2 ml) is heated at 120° C. for 16 hours. The resin is filtered off and washed six times with DMF (3 ml), six times with dimethyl sulfoxide (DMSO) (3 ml), three times with water (3 ml), three times with methanol (3 ml) and four times with methylene chloride (3 ml).

The resin suspended in methylene chloride (1 ml) is then treated with a 6/4 mixture of methylene chloride/trifluoroacetic acid (2 ml) for 1 hour at room temperature.

The medium is filtered and the resin is then washed with methylene chloride. The filtrate is concentrated to dryness (20 mg).

LC/MS: ES+450.3 452.3 454.2. 2 chlorine atoms.

Compounds 6 to 31 were prepared according to protocols similar to those described for the preparation of the compounds of Examples 1 to 5 above.

The structures of compounds 6 to 31 are collated in Table 1 below, in which "Method" specifies the method number (1, 2 or 3 described above) used for the preparation of each compound:

TABLE 1

Structures of compounds 6 to 31

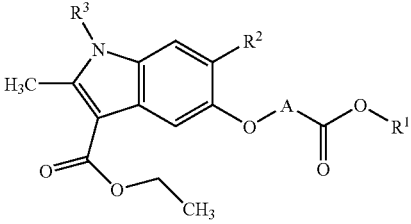

| Ex. No. | $R^1$ | A | $R^2$ | $R^3$ | Method |
|---|---|---|---|---|---|
| 6 | —H | —(CH$_2$)$_3$— | 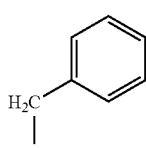 | 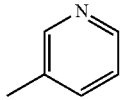 | 3 |
| 7 | —H | —(CH$_2$)$_3$— | 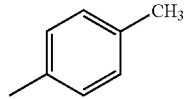 | —H | 3 |
| 8 | —H | —C(CH$_3$)$_2$— | 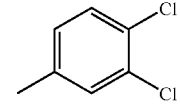 | —H | 3 |
| 9 | —H | —C(CH$_3$)$_2$— | 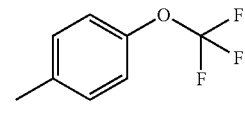 | —H | 3 |
| 10 | —H | —C(CH$_3$)$_2$— | 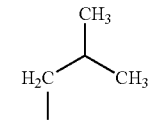 | 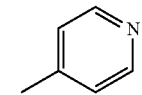 | 3 |
| 11 | —H | —C(CH$_3$)$_2$— | 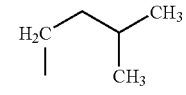 | 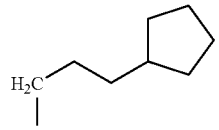 | 3 |
| 12 | —H | —CH$_2$— | 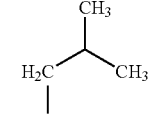 | 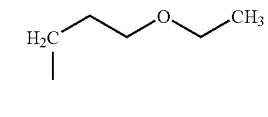 | 1 |
| 13 | —H | —CH$_2$— | 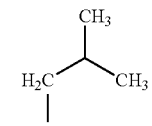 | | 1 |

TABLE 1-continued

Structures of compounds 6 to 31

| Ex. No. | R¹ | A | R² | R³ | Method |
|---|---|---|---|---|---|
| 14 | —H | —CH₂— | (3-cyclopentylpropyl) | —CH₂CH₂OCH₃ | 2 |
| 15 | —H | —CH₂— | —(CH₂)₅—CH₃ | —CH₂CH₂OCH₃ | 2 |
| 16 | —H | —CH₂— | —CH₂-(4-fluorophenyl) | —CH₂CH₂OCH₃ | 2 |
| 17 | —H | —CH₂— | —CH₂CH₂CH₂OCH₂CH₃ | —CH₂CH₂OCH₃ | 2 |
| 18 | —H | —(CH₂)₃— | (3-trifluoromethylphenyl)methyl | —H | 3 |
| 19 | —H | —(CH₂)₃— | (4-trifluoromethylphenyl)methyl | —H | 3 |
| 20 | —H | —(CH₂)₃— | (4-trifluoromethoxyphenyl)methyl | —H | 3 |
| 21 | —H | —(CH₂)₃— | (4-chlorophenyl)methyl | —H | 3 |
| 22 | —H | —C(CH₃)₂— | (benzo[1,3]dioxol-5-yl)methyl | —H | 3 |
| 23 | —H | —C(CH₃)₂— | (3-trifluoromethylphenyl)methyl | —H | 3 |

TABLE 1-continued

Structures of compounds 6 to 31

| Ex. No. | R¹ | A | R² | R³ | Method |
|---|---|---|---|---|---|
| 24 | —H | —C(CH₃)₂— | 4-(trifluoromethyl)benzyl | —H | 3 |
| 25 | —H | —C(CH₃)₂— | 4-(trifluoromethoxy)benzyl | —H | 3 |
| 26 | —H | —C(CH₃)₂— | 2-methoxybenzyl | —H | 3 |
| 27 | —H | —C(CH₃)₂— | 4-methoxybenzyl | —H | 3 |
| 28 | —H | —C(CH₃)₂— | 4-chlorobenzyl | —H | 3 |
| 29 | —H | —(CH₃)₂— | —CH₂CH₂OCH₂CH₃ | —CH₂OCH₃ | 2 |
| 30 | —H | —(CH₃)₂— | —CH₂-(4-fluorophenyl) | —CH₂OCH₃ | 2 |
| 31 | —H | —(CH₃)₂— | —CH₂CH₂-cyclopentyl | —CH₂OCH₃ | 2 |

The results of the analyses of the synthesised products 6 to 31 are given in Table 2 below, in which table:
M represents the theoretical molar mass of the compound;
LC/MS indicates the result of the analysis by mass spectrometry coupled to liquid-phase chromatography; and
NMR indicates the chemical shifts δ (in ppm) of the proton by magnetic resonance at 300 MHz.

TABLE 2

| Example No | M | LC/MS | NMR |
|---|---|---|---|
| 6 | 506.98 | ES+ 507.2/509.2 1 Cl | |
| 7 | 382.41 | ES+ 383.3 | |
| 8 | 395.45 | ES− 394.2 | |
| 9 | 450.32 | ES− 448.1/ 450.1 2 Cl | |
| 10 | 521.53 | ES+ 522.4 | |
| 11 | 452.55 | ES+ 453.4 | |
| 12 | 443.58 | | $^1$H NMR (300 MHz, DMSO-D6), δ ppm: 0.9 (d, J = 6.5 Hz, 6 H); 1.0 (m, 2 H); 1.5 (m, 10 H); 2.1 (m, 1 H); 2.7 (m, 5 H); 3.3 (m, 4 H); 4.0 (d, J = 7.2 Hz, 2 H); 4.2 (q, J = 7.1 Hz, 2 H); 4.7 (s, 2 H); 7.3 (s, 1 H); 7.3 (s, 1 H); 12.9 (s, 1 H). |
| 13 | 419.51 | ES− 418.5 | |
| 14 | 445.55 | ES− 444.4 | $^1$H NMR (300 MHz, chloroform-D), δ ppm: 1.1 (d, J = 6.3 Hz, 2 H); 1.6 (m, 14 H); 2.8 (m, 5 H); 3.3 (s, 3 H); 3.7 (t, J = 5.6 Hz, 2 H); 4.3 (t, J = 5.6 Hz, 2 H); 4.4 (q, J = 7.1 Hz, 2 H); 4.8 (s, 2 H); 7.1 (s, 1 H); 7.5 (s, 1 H). |
| 15 | 419.51 | ES+ 420.3 | |
| 16 | 457.50 | ES− 456.3 | |
| 17 | 421.49 | ES+ 422.3 | $^1$H NMR (300 MHz, chloroform-D), δ ppm: 1.2 (t, J = 7.0 Hz, 3 H); 1.4 (t, J = 7.1 Hz, 3 H); 1.9 (m, 2 H); 2.7 (s, 3 H); 2.9 (t, J = 7.2 Hz, 2 H); 3.3 (s, 3 H); 3.6 (m, 6 H); 4.3 (t, J = 5.6 Hz, 2 H); 4.4 (q, J = 6.9 Hz, 2 H); 4.7 (s, 2 H); 6.8 (s, 1 H); 7.1 (s, 1 H); 7.5 (s, 1 H). |
| 18 | 449.42 | ES+ 450.3 | |
| 19 | 449.42 | ES− 448.4 | |
| 20 | 465.42 | ES− 464.4 | |
| 21 | 415.87 | ES+ 416.3 | |
| 22 | 425.43 | ES− 424.3 | |
| 23 | 449.42 | ES+ 450.4 | |
| 24 | 449.42 | ES+ 450.3 | |
| 25 | 465.42 | ES+ 466.3 | |
| 26 | 411.45 | ES+ 412.4 | |
| 27 | 411.45 | ES+ 412.4 | |
| 28 | 415.87 | ES− 414.3/ 416.3 1 Cl | |
| 29 | 449.54 | ES+ 450.4 | $^1$H NMR (300 MHz, chloroform-D), δ ppm: 1.3 (t, J = 6.8 Hz, 3 H); 1.4 (t, J = 7.0 Hz, 3 H); 1.9 (m, 2 H); 2.2 (m, 2 H); 2.6 (t, J = 6.6 Hz, 2 H); 2.8 (m, 5 H); 3.3 (s, 3 H); 3.6 (m, 6 H); 4.1 (t, J = 5.5 Hz, 2 H); 4.3 (t, J = 5.7 Hz, 2 H); 4.4 (q, J = 7 Hz, 2 H); 7.0 (s, 1 H); 7.6 (s, 1 H). |
| 30 | 485.55 | ES+ 486.4 | $^1$H NMR (300 MHz, chloroform-D), δ ppm: 1.4 (t, J = 7.1 Hz, 2 H); 2.2 (m, 2 H); 2.7 (m, 6 H); 2.9 (m, 4 H); 3.3 (s, 3 H); 3.5 (t, J = 5.7 Hz, 2 H); 4.2 (m, 4 H); 4.4 (q, J = 7.1 Hz, 2 H); 6.0 (s, 1 H); 6.8 (s, 1 H); 6.9 (m,, 2 H); 7.1 (m, 2 H); 7.6 (s, 1 H). |
| 31 | 473.61 | ES+ 474.5 | $^1$H NMR (300 MHz, chloroform-D), δ ppm: 1.5 (m, 16 H); 2.2 (m, 2 H); 2.7 (m, 7 H); 3.3 (s, 3 H); 3.7 (t, J = 5.6 Hz, 2 H); 4.1 (m, 2 H); 4.3 (t, J = 5.7 Hz, 2 H); 4.4 (m, 2 H); 7.0 (s, 1 H); 7.6 (s, 1 H). |

Results

The measurement of the PPAR activation was performed according to a technique described by Lehmann et al. (*J. Biol. Chem.*, 270, (1995), CV-1 cells (monkey kidney cells) are cotransfected with an expression vector for the chimeric protein PPARγ-Gal4 and with a "reporter" plasmid that allows expression of the luciferase gene placed under the control of a promoter comprising Gal4 response elements.

The cells are seeded in 96-well microplates and cotransfected using a commercial reagent with the reporter plasmid (pG5-tk-pGL3) and the expression vector for the chimeric protein (PPARγ-Gal4). After incubation for 4 hours, whole culture medium (comprising 10% foetal calf serum) is added to the wells. After 24 hours, the medium is removed and replaced with whole medium comprising the test products. The products are left in contact with the cells for 18 hours. The cells are then lysed and the luciferase activity is measured using a luminometer. A PPARγ activation factor can then be calculated by means of the activation of the expression of the reporter gene induced by the product (relative to the control cells that have received no product).

In the absence of the PPARγ ligand binding domain (vector expressing Gal4 alone), the luciferase activity measured in the presence of an agonist is zero.

The following transactivation result was obtained with a concentration of 50 μM on PPARγ.

| Ex. | Concentration | Activation factor of the chimeric protein PPARγ-Gal4 |
|---|---|---|
| 4 | 50 μM | 17 |
| Without agonist (Control) | — | 1 |

Example of Biological Activities of Partial Agonists

Transactivation Test

The transactivation test using the expression of a chimeric protein Gal-4-PPARγ makes it possible to determine also whether an agonist functions as a "full" agonist or as a "partial" agonist in this system.

An agonist is "partial" in this system if it induces a weaker response, i.e. it has lower efficacy, than rosiglitazone, which is a "full" agonist. In concrete terms, in our system, the transactivation obtained at the plateau with a partial agonist will be between 20% and 50% of the maximum response (efficacy) at the plateau of rosiglitazone.

| Ex. | Maximum stimulation of the PPARγ chimeric protein obtained with rosiglitazone | Concentration to reach the maximum stimulation of the PPARγ chimeric protein |
|---|---|---|
| 31 | 24% | 1 μM |

The invention claimed is:

1. A compound of formula (1):

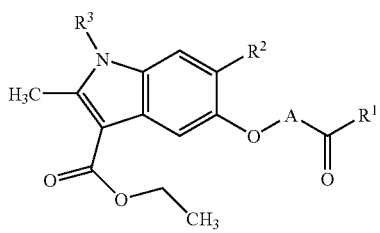

in which:
R$^1$ is —O—R'$^1$ or —NR'$^1$R'''$^1$;
R'$^1$ and R'''$^1$ are each independently H, optionally substituted alkyl having 1 to 10 carbon atoms, optionally substituted alkenyl having 2 to 10 carbon atoms, optionally substituted alkynyl having 2 to 10 carbon atoms, optionally substituted cycloalkyl having 4 to 9 carbon atoms, optionally substituted aryl having 6 to 18 carbon atoms, or optionally substituted heteroaryl;
R$^2$ is optionally substituted alkyl having 1 to 10 carbon atoms, optionally substituted alkenyl having 2 to 10 carbon atoms, or optionally substituted alkynyl having 2 to 10 carbon atoms, aryl having 6 to 18 carbon atoms which is optionally substituted and/or optionally fused to a monocyclic or polycyclic, saturated or unsaturated 5- to 8-membered nucleus optionally containing one or more hetero atoms chosen from O, N and S, and said nucleus is optionally substituted, or a saturated, unsaturated or aromatic, optionally substituted 5- to 8-membered monocyclic heterocyclic radical containing one or more hetero atoms chosen from O, N and S;
R$^3$ is H or optionally substituted alkyl having 1 to 10 carbon atoms; and
A is a linear or branched alkylene chain containing from 1 to 6 carbon atoms;
wherein optionally substituted alkyl groups listed above are each optionally substituted one or more times by halogen, —O-alkyl having 1 to 10 carbon atoms, aryl having 6 to 18 carbon atoms and which is optionally substituted by halogen, methyl, ethyl, methoxy, phenyl, trifluoromethyl or trifluoromethoxy, cycloalkyl having 4 to 9 carbon atoms, or a heterocyclic group;
wherein optionally substituted alkenyl groups listed above are each unsubstituted or substituted one or more times by halogen, trifluoromethyl, trifluoromethoxy, hydroxyl, alkoxy, alkoxycarbonyl, carboxyl or oxo;
wherein optionally substituted alkynyl groups listed above are each unsubstituted or substituted one or more times by halogen, trifluoromethyl, trifluoromethoxy, hydroxyl, alkoxy, alkoxycarbonyl, carboxyl or oxo;
wherein optionally substituted aryl groups listed above are each unsubstituted or substituted one or more times by halogen, methyl, ethyl, methoxy, phenyl, trifluoromethyl or trifluoromethoxy;
wherein optionally substituted heterocyclic groups listed above are each unsubstituted or substituted one or more times by halogen, methyl, ethyl, methoxy, phenyl, trifluoromethyl or trifluoromethoxy;
wherein aromatic heterocyclic groups or heteroaryl groups are selected from pyridyl, pyrimidinyl, triazolyl, thiadiazolyl, oxazolyl, thiazolyl, thienyl, quinolyl, benzothiazolyl, acridinyl, phenazinyl, carbazolyl, and benzothiophenyl;
wherein saturated or unsaturated heterocyclic groups are selected morpholinyl, piperidinyl, thiazolidinyl, oxazolidinyl, tetrahydrothienyl, tetrahydrofuryl, pyrrolidinyl, isoxazolidinyl, imidazolidinyl, and pyrazolidinyl;
or
an optical isomer thereof, an oxide form thereof, or a pharmaceutically acceptable addition salt thereof.

2. A compound according to claim 1, wherein:
R$^1$ is —O—R'$^1$, and R'$^1$ is H or alkyl;
R$^2$ is alkyl optionally substituted by —O-alkyl, aryl or cycloalkyl, or R$^2$ is optionally substituted aryl, or R$^2$ is an optionally substituted heterocyclic radical;
R$^3$ is H, or is alkyl optionally substituted by —O-alkyl, aryl or cycloalkyl; and/or
A is a linear or branched alkylene chain containing from 1 to 6 carbon.

3. A compound according to claim 1, wherein:
R$^1$ is —O—R'$^1$, and R'$^1$ is H or alkyl containing from 1 to 6 carbon atoms;
R$^2$ is alkyl containing from 1 to 6 carbon atoms which is optionally substituted by —O—alkyl containing from 1 to 6 carbon atoms, phenyl, or 5- or 6-membered cycloalkyl, or R$^2$ is optionally substituted phenyl, or R$^2$ is an optionally substituted heterocyclic radical;
R$^3$ is H or alkyl containing from 1 to 6 carbon atoms which is optionally substituted by —O-alkyl containing from 1 to 6 carbon atoms, phenyl, or 5- or 6-membered cycloalkyl;
and/or
A is a linear or branched alkylene chain containing from 1 to 6 carbon atoms.

4. A compound according to claim 1, wherein:
R$^1$ is —O—R'$^1$, and R'$^1$ is H, methyl, or ethyl;
R$^2$ is alkyl containing from 1 to 6 carbon atoms optionally substituted by methoxy, ethoxy, substituted phenyl, cyclopentyl, or cyclohexyl, or $R^2$ is optionally substituted phenyl, or $R^2$ is an optionally substituted aromatic heterocyclic radical containing at least one nitrogen atom;

$R^3$ is H, or is alkyl containing from 1 to 6 carbon atoms which is optionally substituted by methoxy, ethoxy, substituted phenyl, cyclopentyl, or cyclohexyl; and/or A is an alkylene chain of the formula —$(CH_2)_k$—, in which k is 1, 2, 3, 4, 5, or 6, or A is —$C(CH_3)_2$—.

5. A compound according to claim 1, wherein:

$R^1$ is OH;

$R^2$ is methyl, ethyl, propyl, or n-hexyl, in each case optionally substituted by a methoxy, ethoxy, substituted phenyl, or cyclopentyl, or $R^2$ is optionally substituted phenyl, or $R^2$ is optionally substituted pyridyl;

$R^3$ is H, or is methyl, ethyl, propyl, isopropyl, isobutyl, or isopentyl, which in each is optionally substituted by methoxy, ethoxy, or substituted phenyl; and/or A is an alkylene chain of the formula —$(CH_2)_k$—, in which k is 1, 2, or 3, or A is —$C(CH_3)_2$—.

6. A compound according to claim 1, wherein substituents on the aryl and heterocyclic radicals are each halogens, methyl, ethyl, methoxy, phenyl, trifluoromethyl, or trifluoromethoxy.

7. A compound according to claim 1, wherein said heterocyclic radicals are each thienyl, benzothiophenyl, pyridyl, or oxazolyl.

8. A compound according to claim 1, wherein said compound is selected from:

ethyl 1-benzyl-5-(3-carboxypropoxy)-2-methyl6-pyrid-3-yl1H-indole-3-carboxylate;

ethyl 5-(3-carboxypropoxy)-1-(4-chlorobenzyl)-2-methyl-6-pyrid-3-yl-1H-indole-3-carboxylate;

ethyl 5-(1-carboxy-1-methylethoxy)-2-methyl1-(3-methylbutyl)-6-pyrid-4-yl1H-indole-3-carboxylate;

ethyl 5-carboxymethoxy-6-hexyl1 isobutyl2-methyl-1H-indole-3-carboxylate;

ethyl 5-carboxymethoxy-6-(3-ethoxypropyl)-1-isobutyl2-methyl-1H-indole-3-carboxylate;

ethyl 5-carboxymethoxy-6-(3-cyclopentylpropyl)-1-(2-methoxyethyl)-2-methyl-1H-indole-3-carboxylate;

ethyl 5-carboxymethoxy-6-[2-(4-fluorophenyl)ethyl]-1-(2-methoxyethyl)-2-methyl-1H-indole-3-carboxylate;

ethyl 5-(3-carboxypropoxy)-6-hexyl-1-(2-methoxyethyl)-2-methyl-1H-indole-3-carboxylate;

ethyl 5-(3-carboxypropoxy)-6-(3-ethoxypropyl)-1-(2-methoxyethyl)-2-methyl-1H-indole-3-carboxylate; and ethyl 5-(3-carboxypropoxy)-6-(3-cyclopentylpropyl)-1-(2-methoxyethyl)-2-methyl-1H-indole-3-carboxylate; and optical isomers thereof, oxide forms thereof, and pharmaceutically acceptable addition salts thereof with acids or bases.

9. A process for preparation of a compound according to claim 1, said process comprising:

subjecting the hydroxyl function of ethyl 6-bromo-5-hydroxy-2-methyl-1H-indole-3-carboxylate to the action of a compound of formula (2):

Br-A-CO$_2$R  (2)

in which A is as defined and R is a protecting group for the acid function, in the presence of a base, in polar aprotic medium, to give a compound of formula (3):

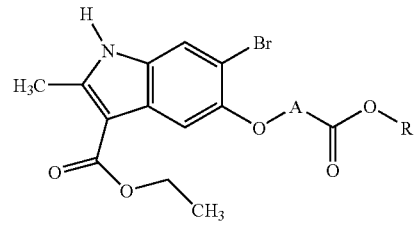
(3)

in which A and R are as defined;

optionally substituting the nitrogen atom of the compound of formula (3) under the action of a bromide $R^3$—Br, in which $R^3$ is as defined, to obtain compound of formula (4):

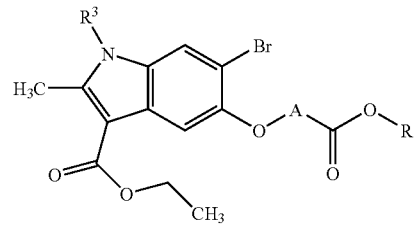
(4)

in which A, $R^3$ and R are as defined;

treating a compound of the formula R'—CH=CH—R" (precursor of the radical $R^2$—) with a borane, to give an $R^2$-borane, in which $R^2$ is as defined coupling the compound $R^2$-borane the compound of formula (3) or formula (4), in the presence of a palladium catalyst, in basic medium, in a polar aprotic solvent, to give a compound of formula ($1_R$):

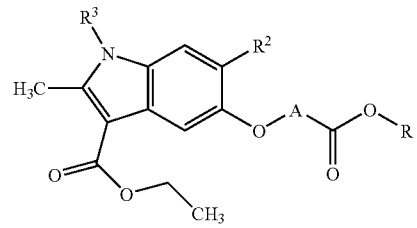
($1_R$)

in which A, $R^2$, $R^3$ and R are as defined;

converting the compound of formula ($1_R$) into the corresponding acid of formula ($1_{OH}$):

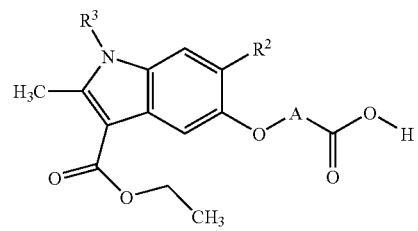
($1_{OH}$)

which is a compound of formula (1) in which $R^1$ is a hydroxyl group; and optionally esterifying the acid or converting the acid into the corresponding amide, to form a compound of formula (1), with $R^1$ other than a hydroxyl group.

10. A process for the preparation of a compound according to claim 1, said process comprising:

subjecting ethyl 6-bromo-5-hydroxy-2-methyl-1H-indole-3-carboxylate, the hydroxyl function of which is protected, to the action of a compound of formula (2):

in which A is as defined and R is a protecting group for the acid function, in the presence of a base, in polar aprotic medium, to give a compound of formula (3):

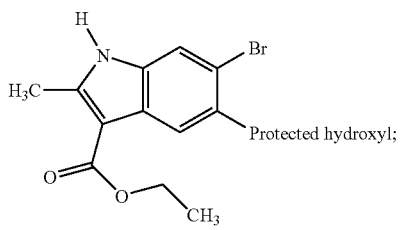

optionally substituting the nitrogen atom of the compound of formula (3) under the action of a bromide $R^3$—Br, in which $R^3$ is as defined, to obtain a compound of formula (4):

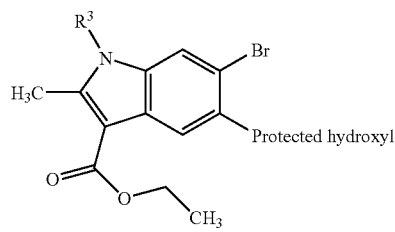

in which $R^3$ is as defined;

deprotecting the hydroxyl function, in basic medium and in the presence of an alcohol, to obtain the compound of formula (5):

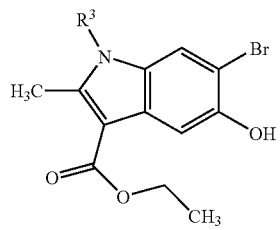

in which $R^3$ is as defined;

placing the compound of formula (5) with a grafted resin of formula (6):

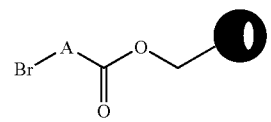

in which A is as defined and ● is the resin support, in basic medium and a polar aprotic solvent, in the presence of potassium iodide, to obtain a compound of formula (7):

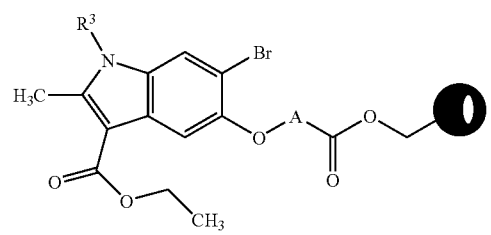

in which A, $R^3$ and ● are as defined;

treating a compound of the formula R'—CH═CH—R" (precursor of the radical $R^2$—) with a borane, to give an $R^2$-borane, in which $R^2$ is as defined;

coupling the compound $R^2$-borane the compound of formula (3) or formula (4), in the presence of a palladium catalyst, in basic medium, in a polar aprotic solvent, to give a compound of formula (8):

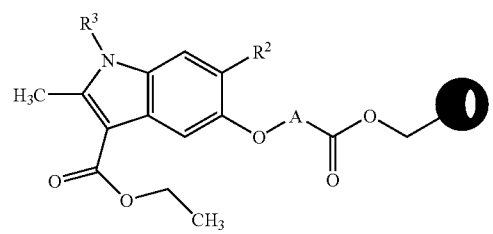

in which A, $R^2$, $R^3$ and ● are as defined;

detaching the grafted compound from the resin support, to give the acid compound of formula ($1_{OH}$):

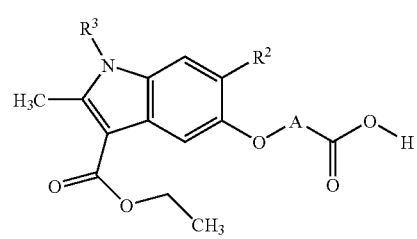

which is a compound of formula (1) in which $R^1$ is a hydroxyl group; and optionally esterifying the acid compound or converting the acid compound into the corresponding amide, to form a compound of formula (1) with $R^1$ other than a hydroxyl group.

11. A process for the preparation of a compound according to claim 1, said process comprising:

grafting ethyl 6-bromo-5-hydroxy-2-methyl-1H-indole-3-carboxylate onto a resin support, to obtain the bromo derivative of formula (9):

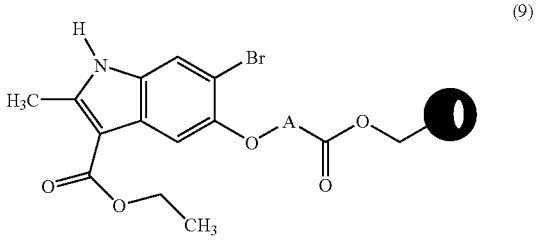

(9)

in which A is as defined and ● is the resin support;

optionally substituting the nitrogen atom of the derivative of formula (9) under the action of a bromide $R^3$—Br, in which $R^3$ is as defined, to obtain a compound of the formula:

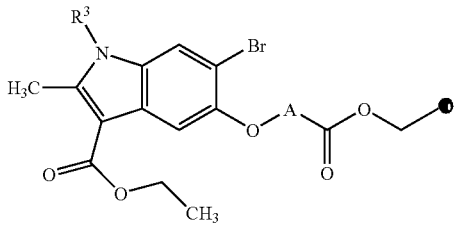

in which $R^3$ is as defined;

before or after the optional substitution of the nitrogen atom of the derivative of formula (9), treating a compound of the formula R'—CH═CH—R" (precursor of the radical $R^2$—) with a borane, to give an $R^2$-borane, in which $R^2$ is as defined, and coupling the compound $R^2$-borane to the derivative of formula (9) or the N-substituted derivative thereof, in the presence of a palladium catalyst, in basic medium, in a polar aprotic solvent;

detaching the grafted compound from the resin support, to give the acid compound of formula ($1_{OH}$):

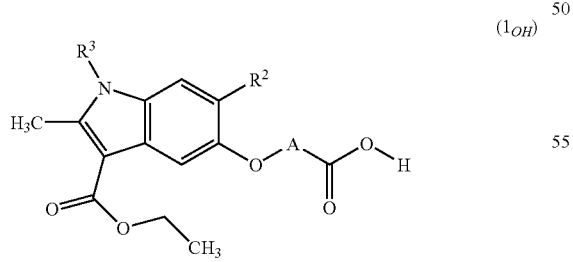

($1_{OH}$)

which is a compound of formula (1) in which $R^1$ is a hydroxyl group; and optionally esterifying the acid compound or converting the acid compound into the corresponding amide, to form a compound of formula (1) with $R^1$ other than a hydroxyl group.

12. A pharmaceutical composition comprising a pharmaceutically effective amount of at least one compound according to claim 1, and one or more pharmaceutically acceptable vehicles.

13. A method for the treatment of dyslipidaemia, atherosclerosis, or type 2 diabetes comprising administering to a patient an effective amount of a compound of claim 1.

14. A compound according to claim 1, wherein
$R^1$ is —O—$R'^1$,
$R'^1$ is H or alky having 1 to 10 carbon atoms;
$R^2$ is alkyl having 1 to 10 carbon atoms which is optionally substituted by —O-alkyl having 1 to 10 carbon atoms, aryl having 6 to 18 carbon atoms or cycloalkyl having 4 to 9 carbon atoms optionally containing one or more double and/or triple bonds, or $R^2$ is aryl having 6 to 18 carbon atoms which is optionally substituted by halogens, methyl, ethyl, methoxy, phenyl, trifluoromethyl, or trifluoromethoxy, or $R^2$ is a heterocyclic group selected from thienyl, benzothiophenyl, pyridyl and oxazolyl, which in each case is which is optionally substituted by halogens, methyl, ethyl, methoxy, phenyl, trifluoromethyl, or trifluoromethoxy; and
$R^3$ is H, or is alkyl having 1 to 10 carbon atoms which is optionally substituted by —O-alkyl having 1 to 10 carbon atoms, aryl having 6 to 18 carbon atoms or cycloalkyl having 4 to 9 carbon atoms optionally containing one or more double and/or triple bonds.

15. A compound according to claim 1, wherein
$R^1$ is —O—$R'^1$;
$R'^1$ is H or alkyl having 1 to 10 carbon atoms;
$R^2$ is alkyl having 1 to 10 carbon atoms optionally substituted by —O-alkyl having 1 to 10 carbon atoms, aryl having 6 to 18 carbon atoms, or cycloalkyl having 4 to 9 carbon atoms, or $R^2$ is aryl having 6 to 18 carbon atoms which is optionally substituted by halogens, methyl, ethyl, methoxy, phenyl, trifluoromethyl, or trifluoromethoxy, or $R^2$ is a heterocyclic radical which is optionally substituted by halogens, methyl, ethyl, methoxy, phenyl, trifluoromethyl, or trifluoromethoxy;
$R^3$ is H, or is alkyl having 1 to 10 carbon atoms optionally substituted by —O-alkyl having 1 to 10 carbon atoms, aryl having 6 to 18 carbon atoms, or cycloalkyl having 4 to 9 carbon atoms; and
A is a linear or branched alkylene chain containing from 1 to 6 carbon atoms.

16. A compound according to claim 15, wherein
$R^1$ is —O—$R'^1$;
$R'^1$ is H or alkyl having 1 to 6 carbon atoms;
$R^2$ is alkyl which is optionally substituted by —O-alkyl containing from 1 to 6 carbon atoms, 5- or 6-membered cycloalkyl, or phenyl which is substituted by halogens, methyl, ethyl, methoxy, phenyl, trifluoromethyl, or trifluoromethoxy, or $R^2$ is phenyl which is optionally substituted by halogens, methyl, ethyl, methoxy, phenyl, trifluoromethyl, or trifluoromethoxy, or $R^2$ is a heterocyclic radical which is optionally substituted by halogens, methyl, ethyl, methoxy, phenyl, trifluoromethyl, or trifluoromethoxy;
$R^3$ is H or is alkyl which is optionally substituted by —O-alkyl containing from 1 to 6 carbon atoms, phenyl, or 5- or 6-membered cycloalkyl; and
A is a linear or branched alkylene chain containing from 1 to 6 carbon atoms.

17. A compound according to claim 16, wherein
$R^1$ is —O—$R'^1$;
$R'^1$ is H, methyl, or ethyl;
$R^2$ is alkyl having 1 to 6 carbon atoms which is optionally substituted by methoxy, ethoxy, cyclopentyl, cyclohexyl, or phenyl which is substituted by halogens, methyl, ethyl, methoxy, phenyl, trifluoromethyl, or trifluoromethoxy, or $R^2$ is phenyl which is optionally substituted by halogens, methyl, ethyl, methoxy, phenyl, trifluoromethyl, or trifluoromethoxy, or $R^2$ is an aromatic heterocyclic radical containing at least one nitrogen atom which is optionally substituted by halogens, methyl, ethyl, methoxy, phenyl, trifluoromethyl, or trifluoromethoxy;

$R^3$ is H, or alkyl having 1 to 6 carbon atoms which is optionally substituted by methoxy, ethoxy, cyclopentyl, cyclohexyl, or phenyl which is substituted by halogens, methyl, ethyl, methoxy, phenyl, trifluoromethyl, or trifluoromethoxy; and A is an alkylene chain of the formula —$(CH_2)_k$—, in which k is 1, 2, 3, 4, 5, or 6, or A is —$C(CH_3)_2$—.

18. A compound according to claim 16, wherein $R^1$ is OH;

$R^2$ is methyl, ethyl, propyl, or n-hexyl, which in each case is optionally substituted by methoxy, ethoxy, cyclopentyl, cyclohexyl, or phenyl which is substituted by halogens, methyl, ethyl, methoxy, phenyl, trifluoromethyl, or trifluoromethoxy, or $R^2$ is phenyl which is optionally substituted by halogens, methyl, ethyl, methoxy, phenyl, trifluoromethyl, or trifluoromethoxy, or $R^2$ is pyridyl which is optionally substituted by halogens, methyl, ethyl, methoxy, phenyl, trifluoromethyl, or trifluoromethoxy;

$R^3$ is H, or is methyl, ethyl, propyl, isopropyl, isobutyl, or isopentyl, which in each is optionally substituted by methoxy, ethoxy, or phenyl which is substituted by halogens, methyl, ethyl, methoxy, phenyl, trifluoromethyl, or trifluoromethoxy; and A is an alkylene chain of the formula —$(CH_2)_k$—, in which k is 1, 2, or 3, or A is —$C(CH_3)_2$—.

19. A compound according to claim 1, wherein said compound is a salt of a compound of formula (1) and a chiral amine or chiral acid, wherein said chiral amine is quinine, brucine, (S)-1-(benzyloxymethyl)propylamine (III), (−)-ephedrine, (4S,5R)-(+)-1,2,3,4-tetramethyl-5-phenyl-1,3-oxazolidine, (R)-1-phenyl-2-p-tolylethylamine, (S)-phenylglycinol, (−)-N-methylephedrine, (+)-(2S,3R)-4-dimethylamino-3-methyl-1,2-diphenyl-2-butanol, (S)-phenylglycinol, or (S)-α-methylbenzylamine, or a mixture of two or more thereof; and said chiral acid is (+)-d-di-O-benzoyltartaric acid, (−)-1-di-O-benzoyltartaric acid, (−)-di-O,O'-p-toluyl1-tartaric acid, (+)-di-O,O '-p-toluyl-d-tartaric acid, (R)-(+)-malic acid, (S)-(−)-malic acid, (+)-camphanic acid, (−)-camphanic acid, R-(−)-1,1'-binaphthalene-2,2'-diyl hydrogen phosphate, (S)-(+)-1,1'-binaphthalene-2,2'-diyl hydrogen phosphate, (+)-camphoric acid, (−)-camphoric acid, (S)-(+)-2-phenylpropionic acid, (R)-(−)-2-phenylpropionic acid, d-(−)-mandelic acid, 1-(+)-mandelic acid, d-tartaric acid, or 1-tartaric acid, or a mixture of two or more thereof.

20. A compound according to claim 1, wherein A is >CH($CH_3$), >C($CH_3$)$_2$, —$CH_2$—CH($CH_3$)—$CH_2$—, —$CH_2$—C($CH_3$)$_2$—$CH_2$—, or —$(CH_2)_k$— chains in which k is an integer chosen from 2, 3, 4, 5 and 6.

21. A compound according to claim 1, wherein A is —$CH_2$—$CH_2$—, —$CH_2$—$CH_2$—$CH_2$—, or —$CH_2$—CH($CH_3$)—$CH_2$—.

22. A compound according to claim 1, wherein $R^2$ is alkyl having 2 to 6 carbon atoms and which is optionally substituted by —O-alkyl having 1 to 6 carbon atoms, 5- or 6-membered cycloalkyl, or phenyl which is substituted by halogens, methyl, ethyl, methoxy, phenyl, trifluoromethyl, or trifluoromethoxy;

phenyl which is unsubstituted or substituted one or more times by halogen, methyl, ethyl, methoxy, phenyl, trifluoromethyl or trifluoromethoxy; or a heteroaryl group selected from quinolyl, pyridyl, benzothiazolyl, triazolyl, thienyl, benzothiophenyl, and oxazolyl, and which is unsubstituted or substituted one or more times by halogen, methyl, ethyl, methoxy, phenyl, trifluoromethyl or trifluoromethoxy.

23. A compound according to claim 22, wherein $R^2$ is alkyl having 2 to 6 carbon atoms and which is optionally substituted by —O-alkyl having 1 to 6 carbon atoms;

phenyl which is unsubstituted or substituted one or more times by halogen, methyl, ethyl, methoxy, phenyl, trifluoromethyl or trifluoromethoxy; or a heteroaryl group selected from quinolyl, pyridyl, benzothiazolyl, triazolyl, thienyl, benzothiophenyl, and oxazolyl, and which is unsubstituted or substituted one or more times by halogen, methyl, ethyl, methoxy, phenyl, trifluoromethyl or trifluoromethoxy.

24. A compound according to claim 1, wherein $R^2$ is pyridyl, hexyl, 3-ethoxypropyl, 3-cyclopentylpropyl, or 2-(4-fluorophenyl)ethyl.

25. A compound according to claim 1, wherein —O-A-CO—$R^1$ is 3-carboxypropoxy, 1-carboxy-l-methylethoxy, or carboxymethoxy.

* * * * *

UNITED STATES PATENT AND TRADEMARK OFFICE
CERTIFICATE OF CORRECTION

PATENT NO. : 7,754,740 B2
APPLICATION NO. : 11/813922
DATED : July 13, 2010
INVENTOR(S) : Adje et al.

It is certified that error appears in the above-identified patent and that said Letters Patent is hereby corrected as shown below:

Column 29, line 31, reads, "ethyl 1-benzyl-5-(3-carboxypropoxy)-2-methyl6-pyrid 3-" SHOULD READ -- ethyl 1-benzyl-5-(3-carboxypropoxy)-2-methyl-6-pyrid 3- --

Column 29, line 32, reads, "yl1H-indole-3-carboxylate;" SHOULD READ -- yl-1H-indole-3-carboxylate --

Column 29, line 35, reads, "ethyl 5-(1-carboxy-1-methylethoxy)-2-methyl1-(3-meth-" SHOULD READ -- ethyl 5-(1-carboxy-1-methylethoxy)-2-methyl-1-(3-meth- --

Column 29, line 36, reads, "ylbutyl)-6-pyrid-4-yl1H-indole-3-carboxylate;" SHOULD READ -- ylbutyl)-6-pyrid-4-yl-1H-indole-3-carboxylate; --

Column 29, line 37, reads, "ethyl 5-carboxymethoxy-6-hexyl1 isobutyl2 methyl-1H-" SHOULD READ -- ethyl 5-carboxymethoxy-6-hexyl-1-isobutyl-2 methyl-1H- --

Column 29, line 39, reads, "ethyl 5-carboxymethoxy-6-(3-ethoxypropyl)-1-isobutyl2-" SHOULD READ -- ethyl 5-carboxymethoxy-6-(3-ethoxypropyl)-1-isobutyl-2- --

Signed and Sealed this

Twenty-first Day of December, 2010

David J. Kappos
*Director of the United States Patent and Trademark Office*